(12) United States Patent
Stokes et al.

(10) Patent No.: US 10,687,819 B2
(45) Date of Patent: Jun. 23, 2020

(54) CLAMPING MECHANISM FOR LINEAR SURGICAL STAPLER

(71) Applicant: ETHICON LLC, Guaynabo, PR (US)

(72) Inventors: Michael J. Stokes, Cincinnati, OH (US); Chester O. Baxter, III, Loveland, OH (US); Matthew S. Corbin, Loveland, OH (US); Disha V. Labhasetwar, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 173 days.

(21) Appl. No.: 15/889,390

(22) Filed: Feb. 6, 2018

(65) Prior Publication Data

US 2019/0239885 A1     Aug. 8, 2019

(51) Int. Cl.
*A61B 17/072*     (2006.01)
*A61B 17/115*     (2006.01)
(Continued)

(52) U.S. Cl.
CPC ...... *A61B 17/115* (2013.01); *A61B 17/07207* (2013.01); *A61B 17/1114* (2013.01);
(Continued)

(58) Field of Classification Search
CPC . A61B 17/068; A61B 17/0644; A61B 17/072; A61B 17/07207; A61B 17/29; A61B 2017/07214; A61B 2017/07271; A61B 2017/0046; A61B 2017/00477; A61B 2017/07285
(Continued)

(56) References Cited

U.S. PATENT DOCUMENTS

| 960,300 A | 6/1910 | Fischer |
|---|---|---|
| 3,078,465 A | 2/1963 | Bobrov |

(Continued)

FOREIGN PATENT DOCUMENTS

| DE | 38 19 292 C1 | 7/1989 |
|---|---|---|
| EP | 0033548 B1 | 5/1986 |

(Continued)

OTHER PUBLICATIONS

U.S. Appl. No. 15/889,363, filed Feb. 6, 2018.
(Continued)

*Primary Examiner* — Scott A Smith
(74) *Attorney, Agent, or Firm* — Frost Brown Todd LLC

(57) ABSTRACT

A surgical stapler includes an anvil channel member, an anvil surface, and a cartridge channel member that releasably couples with the anvil channel member and includes a distal portion that receives a staple cartridge. The stapler further includes first and second latch features. The second latch feature moves between an open position and a closed position in which it engages the first latch feature and fixes the channel members together. A latch lockout member of the stapler is movable between a lockout state in which the lockout member locks the second latch feature in the open position, and a release state in which the lockout member permits the second latch feature to move to the closed position. The latch lockout member is configured to move from the lockout state to the release state in response to being engaged by the first latch feature.

20 Claims, 21 Drawing Sheets

(51) Int. Cl.
*A61B 17/11* (2006.01)
*A61B 90/00* (2016.01)
*A61B 17/00* (2006.01)

(52) U.S. Cl.
CPC .............. *A61B 2017/00367* (2013.01); *A61B 2017/00407* (2013.01); *A61B 2017/00477* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01); *A61B 2090/034* (2016.02); *A61B 2090/0801* (2016.02); *A61B 2090/0811* (2016.02); *A61B 2090/0814* (2016.02)

(58) Field of Classification Search
USPC .. 227/19, 175.2, 176.1, 175.1, 175.3, 180.1; 606/139, 153, 219
See application file for complete search history.

(56) References Cited

U.S. PATENT DOCUMENTS

| | | | |
|---|---|---|---|
| 3,079,606 | A | 3/1963 | Bobrov et al. |
| 3,315,863 | A | 4/1967 | O'Dea |
| 3,317,105 | A | 5/1967 | Astafjev et al. |
| 3,490,675 | A | 1/1970 | Green et al. |
| 4,111,206 | A | 9/1978 | Vishnevsky et al. |
| 4,241,861 | A | 12/1980 | Fleischer |
| 4,290,542 | A | 9/1981 | Fedotov et al. |
| D272,851 | S | 2/1984 | Green et al. |
| D272,852 | S | 2/1984 | Green et al. |
| 4,429,695 | A | 2/1984 | Green |
| 4,520,817 | A | 6/1985 | Green |
| 4,596,351 | A | 6/1986 | Fedotov et al. |
| 4,605,001 | A | 8/1986 | Rothfuss et al. |
| D285,836 | S | 9/1986 | Hunt et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,869,415 | A | 9/1989 | Fox |
| 4,892,244 | A | 1/1990 | Fox et al. |
| 4,955,898 | A | 9/1990 | Matsutani et al. |
| 5,065,929 | A | 11/1991 | Schulze et al. |
| 5,083,695 | A | 1/1992 | Foslien et al. |
| 5,129,570 | A | 7/1992 | Schulze et al. |
| 5,141,144 | A | 8/1992 | Foslien et al. |
| 5,156,614 | A | 10/1992 | Green et al. |
| 5,173,133 | A | 12/1992 | Morin et al. |
| 5,180,092 | A * | 1/1993 | Crainich .......... A61B 17/07207 227/180.1 |
| 5,188,274 | A * | 2/1993 | Moeinzadeh .... A61B 17/07207 227/180.1 |
| 5,221,036 | A | 6/1993 | Takase |
| 5,395,034 | A * | 3/1995 | Allen .............. A61B 17/07207 227/178.1 |
| 5,417,361 | A | 5/1995 | Williamson, IV |
| 5,445,304 | A | 8/1995 | Plyley et al. |
| 5,452,837 | A | 8/1995 | Williamson, IV et al. |
| 5,465,896 | A | 11/1995 | Allen et al. |
| 5,489,058 | A | 2/1996 | Plyley et al. |
| 5,505,363 | A | 4/1996 | Green et al. |
| 5,535,935 | A | 7/1996 | Vidal et al. |
| 5,542,594 | A | 8/1996 | McKean et al. |
| 5,562,241 | A | 10/1996 | Knodel et al. |
| 5,586,711 | A | 12/1996 | Plyley et al. |
| 5,636,779 | A | 6/1997 | Palmer |
| 5,651,491 | A | 7/1997 | Heaton et al. |
| 5,653,373 | A | 8/1997 | Green et al. |
| 5,655,698 | A | 8/1997 | Yoon |
| 5,657,921 | A | 8/1997 | Young et al. |
| 5,673,842 | A | 10/1997 | Bittner et al. |
| 5,680,983 | A | 10/1997 | Plyley et al. |
| 5,718,359 | A | 2/1998 | Palmer et al. |
| 5,785,232 | A | 7/1998 | Vidal et al. |
| 5,816,471 | A | 10/1998 | Plyley et al. |
| 5,871,135 | A | 2/1999 | Williamson, IV et al. |
| 5,893,506 | A * | 4/1999 | Powell ................. A61B 17/072 227/175.1 |
| 5,908,427 | A | 6/1999 | McKean et al. |
| 5,988,479 | A | 11/1999 | Palmer |
| 6,045,560 | A | 4/2000 | McKean et al. |
| 6,131,789 | A | 10/2000 | Schulze et al. |
| 6,155,473 | A | 12/2000 | Tompkins et al. |
| 6,206,903 | B1 | 3/2001 | Ramans |
| 7,032,799 | B2 | 4/2006 | Viola et al. |
| 7,055,730 | B2 | 6/2006 | Ehrenfels et al. |
| 7,121,446 | B2 | 10/2006 | Arad et al. |
| 7,140,527 | B2 | 11/2006 | Ehrenfels et al. |
| 7,188,758 | B2 | 3/2007 | Viola et al. |
| 7,207,471 | B2 | 4/2007 | Heinrich et al. |
| 7,210,609 | B2 | 5/2007 | Leiboff et al. |
| 7,238,195 | B2 | 7/2007 | Viola |
| 7,278,563 | B1 | 10/2007 | Green |
| 7,293,685 | B2 | 11/2007 | Ehrenfels et al. |
| 7,326,232 | B2 | 2/2008 | Viola et al. |
| 7,334,717 | B2 | 2/2008 | Rethy et al. |
| 7,407,078 | B2 | 8/2008 | Shelton, IV et al. |
| 7,419,081 | B2 | 9/2008 | Ehrenfels et al. |
| 7,422,139 | B2 | 9/2008 | Shelton, IV et al. |
| 7,431,730 | B2 | 10/2008 | Viola |
| 7,472,815 | B2 | 1/2009 | Shelton, IV et al. |
| 7,472,816 | B2 | 1/2009 | Holsten et al. |
| 7,490,749 | B2 | 2/2009 | Schall et al. |
| 7,543,729 | B2 | 6/2009 | Ivanko |
| 7,568,604 | B2 | 8/2009 | Ehrenfels et al. |
| 7,571,845 | B2 | 8/2009 | Viola |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,637,410 | B2 | 12/2009 | Marczyk |
| 7,641,091 | B2 | 1/2010 | Olson et al. |
| 7,665,647 | B2 | 2/2010 | Shelton, IV et al. |
| 7,717,312 | B2 | 5/2010 | Beetel |
| 7,721,933 | B2 | 5/2010 | Ehrenfels et al. |
| 7,722,610 | B2 | 5/2010 | Viola et al. |
| 7,740,160 | B2 | 6/2010 | Viola |
| 7,744,628 | B2 | 6/2010 | Viola |
| 7,766,209 | B2 | 8/2010 | Baxter, III et al. |
| 7,810,691 | B2 | 10/2010 | Boyden et al. |
| 7,815,092 | B2 | 10/2010 | Whitman et al. |
| 7,828,189 | B2 | 11/2010 | Holsten et al. |
| 7,837,081 | B2 | 11/2010 | Holsten et al. |
| 7,866,528 | B2 | 1/2011 | Olson et al. |
| 7,905,381 | B2 | 3/2011 | Baxter, III et al. |
| 7,931,182 | B2 | 4/2011 | Boyden et al. |
| 7,942,300 | B2 | 5/2011 | Rethy et al. |
| 7,954,685 | B2 | 6/2011 | Viola |
| 7,954,686 | B2 | 6/2011 | Baxter, III et al. |
| 7,997,469 | B2 | 8/2011 | Olson et al. |
| 8,006,888 | B2 | 8/2011 | Viola |
| 8,028,884 | B2 | 10/2011 | Sniffin et al. |
| 8,070,035 | B2 | 12/2011 | Holsten et al. |
| 8,074,861 | B2 | 12/2011 | Ehrenfels et al. |
| 8,091,754 | B2 | 1/2012 | Ehrenfels et al. |
| 8,113,407 | B2 | 2/2012 | Holsten et al. |
| 8,127,975 | B2 | 3/2012 | Olson et al. |
| 8,141,762 | B2 * | 3/2012 | Bedi ................. A61B 17/0644 227/176.1 |
| 8,152,041 | B2 | 4/2012 | Kostrzewski |
| 8,157,153 | B2 | 4/2012 | Shelton, IV et al. |
| 8,205,781 | B2 * | 6/2012 | Baxter, III ....... A61B 17/07207 227/176.1 |
| 8,231,040 | B2 | 7/2012 | Zemlok et al. |
| 8,245,901 | B2 | 8/2012 | Stopek |
| 8,256,655 | B2 | 9/2012 | Sniffin et al. |
| 8,257,634 | B2 | 9/2012 | Scirica |
| 8,267,300 | B2 | 9/2012 | Boudreaux |
| 8,272,552 | B2 | 9/2012 | Holsten et al. |
| 8,292,146 | B2 | 10/2012 | Holsten et al. |
| 8,292,148 | B2 | 10/2012 | Viola |
| 8,308,043 | B2 | 11/2012 | Bindra et al. |

(56) References Cited

U.S. PATENT DOCUMENTS

| | | |
|---|---|---|
| 8,336,753 B2 | 12/2012 | Olson et al. |
| 8,348,129 B2 | 1/2013 | Bedi et al. |
| 8,418,907 B2 | 4/2013 | Johnson et al. |
| 8,453,908 B2 * | 6/2013 | Bedi ............ A61B 17/0644 227/176.1 |
| 8,464,922 B2 | 6/2013 | Marczyk |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,505,801 B2 | 8/2013 | Ehrenfels et al. |
| 8,544,712 B2 | 10/2013 | Jankowski |
| 8,579,178 B2 | 11/2013 | Holsten et al. |
| 8,636,193 B2 | 1/2014 | Whitman et al. |
| 8,636,939 B2 | 1/2014 | Czernik et al. |
| 8,679,156 B2 | 3/2014 | Smith et al. |
| 8,708,210 B2 | 4/2014 | Zemlok et al. |
| 8,728,118 B2 | 5/2014 | Hinman et al. |
| 8,789,740 B2 | 7/2014 | Baxter, III et al. |
| 8,905,287 B2 | 12/2014 | Racenet et al. |
| 8,915,930 B2 | 12/2014 | Huitema et al. |
| 9,016,541 B2 | 4/2015 | Viola et al. |
| 9,119,617 B2 | 9/2015 | Souls et al. |
| 9,155,537 B2 * | 10/2015 | Katre ............ A61B 17/072 |
| 9,289,209 B2 * | 3/2016 | Gurumurthy .... A61B 17/07207 |
| 9,364,219 B2 | 6/2016 | Olson et al. |
| 9,402,629 B2 | 8/2016 | Ehrenfels et al. |
| 9,439,649 B2 | 9/2016 | Shelton, IV et al. |
| 9,451,959 B2 | 9/2016 | Patankar et al. |
| 9,474,525 B2 | 10/2016 | Smith et al. |
| 9,498,213 B2 | 11/2016 | Marczyk et al. |
| 9,561,030 B2 | 2/2017 | Zhang et al. |
| 9,629,812 B2 | 4/2017 | Widenhouse et al. |
| 9,636,113 B2 | 5/2017 | Wenchell |
| 9,636,128 B2 | 5/2017 | Zemlok et al. |
| 9,681,873 B2 | 6/2017 | Smith et al. |
| 9,693,775 B2 | 7/2017 | Agarwal et al. |
| 9,750,502 B2 | 9/2017 | Scirica et al. |
| 9,867,616 B2 | 1/2018 | Marczyk |
| 2006/0180633 A1 | 8/2006 | Emmons |
| 2007/0119901 A1 | 5/2007 | Ehrenfels et al. |
| 2007/0145096 A1 | 6/2007 | Viola et al. |
| 2009/0255974 A1 | 10/2009 | Viola |
| 2009/0308907 A1 | 12/2009 | Nalagatla et al. |
| 2010/0133317 A1 | 6/2010 | Shelton, IV et al. |
| 2011/0290856 A1 | 12/2011 | Shelton, IV et al. |
| 2012/0046689 A1 | 2/2012 | Criscuolo et al. |
| 2012/0286022 A1 | 11/2012 | Olson et al. |
| 2013/0186935 A1 | 7/2013 | Edoga et al. |
| 2013/0190732 A1 | 7/2013 | Slisz et al. |
| 2014/0103091 A1 | 4/2014 | Whitman et al. |
| 2015/0327855 A1 | 11/2015 | Katre et al. |
| 2016/0157890 A1 | 6/2016 | Drake et al. |
| 2016/0262756 A1 | 9/2016 | Patankar et al. |

FOREIGN PATENT DOCUMENTS

| | | |
|---|---|---|
| EP | 0178940 B1 | 1/1991 |
| EP | 0669104 A1 | 8/1995 |
| EP | 0770355 A1 | 5/1997 |
| EP | 1382303 B1 | 6/2006 |
| EP | 1702567 A2 | 9/2006 |
| EP | 1728475 A2 | 12/2006 |
| EP | 1977701 B1 | 12/2011 |
| EP | 2452636 A2 | 5/2012 |
| EP | 2305137 B1 | 12/2012 |
| EP | 2308390 B1 | 12/2012 |
| EP | 1693007 B1 | 10/2013 |
| EP | 1862129 B1 | 4/2014 |
| EP | 2550920 B1 | 1/2015 |
| EP | 2532313 B1 | 4/2016 |
| EP | 2532312 B1 | 12/2016 |
| EP | 3155988 A1 | 4/2017 |
| GB | 927936 A | 6/1963 |
| JP | 2001-502575 A | 2/2001 |
| JP | 2007-000657 A | 1/2007 |
| SU | 599799 A1 | 4/1978 |
| WO | WO 1999/045849 A1 | 9/1999 |
| WO | WO 2002/030297 A2 | 4/2002 |
| WO | WO 2003/030742 A2 | 4/2003 |
| WO | WO 2003/094743 A1 | 11/2003 |
| WO | WO 2003/094745 A1 | 11/2003 |
| WO | WO 2003/094746 A1 | 11/2003 |
| WO | WO 2003/094747 A1 | 11/2003 |
| WO | WO 2003/079909 A3 | 3/2004 |
| WO | WO 2004/032763 A2 | 4/2004 |
| WO | WO 2007/127283 A2 | 11/2007 |
| WO | WO 2015/065485 A1 | 5/2015 |

OTHER PUBLICATIONS

U.S. Appl. No. 15/889,370, filed Feb. 6, 2018.
U.S. Appl. No. 15/889,374, filed Feb. 6, 2018.
U.S. Appl. No. 15/889,376, filed Feb. 6, 2018.
U.S. Appl. No. 15/889,388, filed Feb. 6, 2018.
European Search Report, Extended, and Written Opinion dated Jun. 24, 2019 for Application No. EP 19155567.1, 9 pgs.
International Search Report and Written Opinion dated May 13, 2019 for Application No. PCT/IB2019/050361, 15 pgs.

* cited by examiner

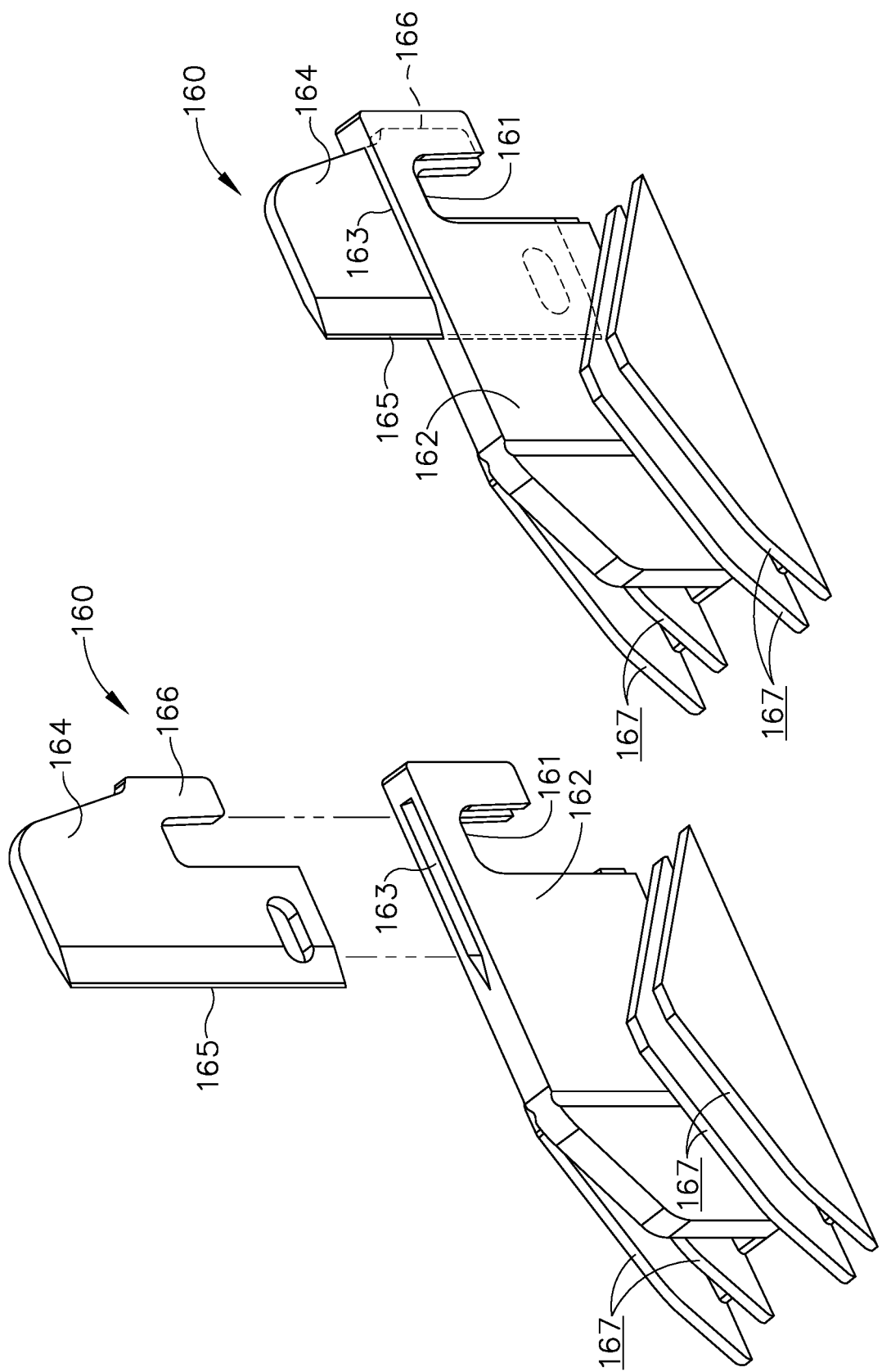

CLAMPING MECHANISM FOR LINEAR SURGICAL STAPLER

BACKGROUND

In some surgical operations, such as a gastrointestinal anastomosis, it may be desirable to clamp down on one or more layers of tissue, cut through the clamped layers of tissue and drive staples through the layers of tissue to substantially seal the severed layers of tissue together near the severed ends of the tissue layers. One such instrument that may be used in such operations is a linear cutting stapler. A linear cutting stapler generally includes a first jaw, a second jaw, a lever for clamping the first jaw relative to the second jaw, an anvil associated with either the first jaw or the second jaw, a staple cartridge associated with the jaw opposing the staple anvil, and a firing assembly movable relative to the rest of the linear cutting stapler. Typically, the first jaw and the second jaw may pivot relative each other in order to grasp tissue between the jaws. Staples are arranged in the staple cartridge such that a portion of firing assembly may actuate through the staple cartridge to drive staples out of staple cartridge, through tissue, and against anvil while also severing tissue captured between the staple cartridge and the staple anvil.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts an exploded view of a staple sled assembly of the surgical stapling instrument of FIG. 1;

FIG. 8 depicts a perspective view of the staple sled assembly of FIG. 7;

Figure 1:
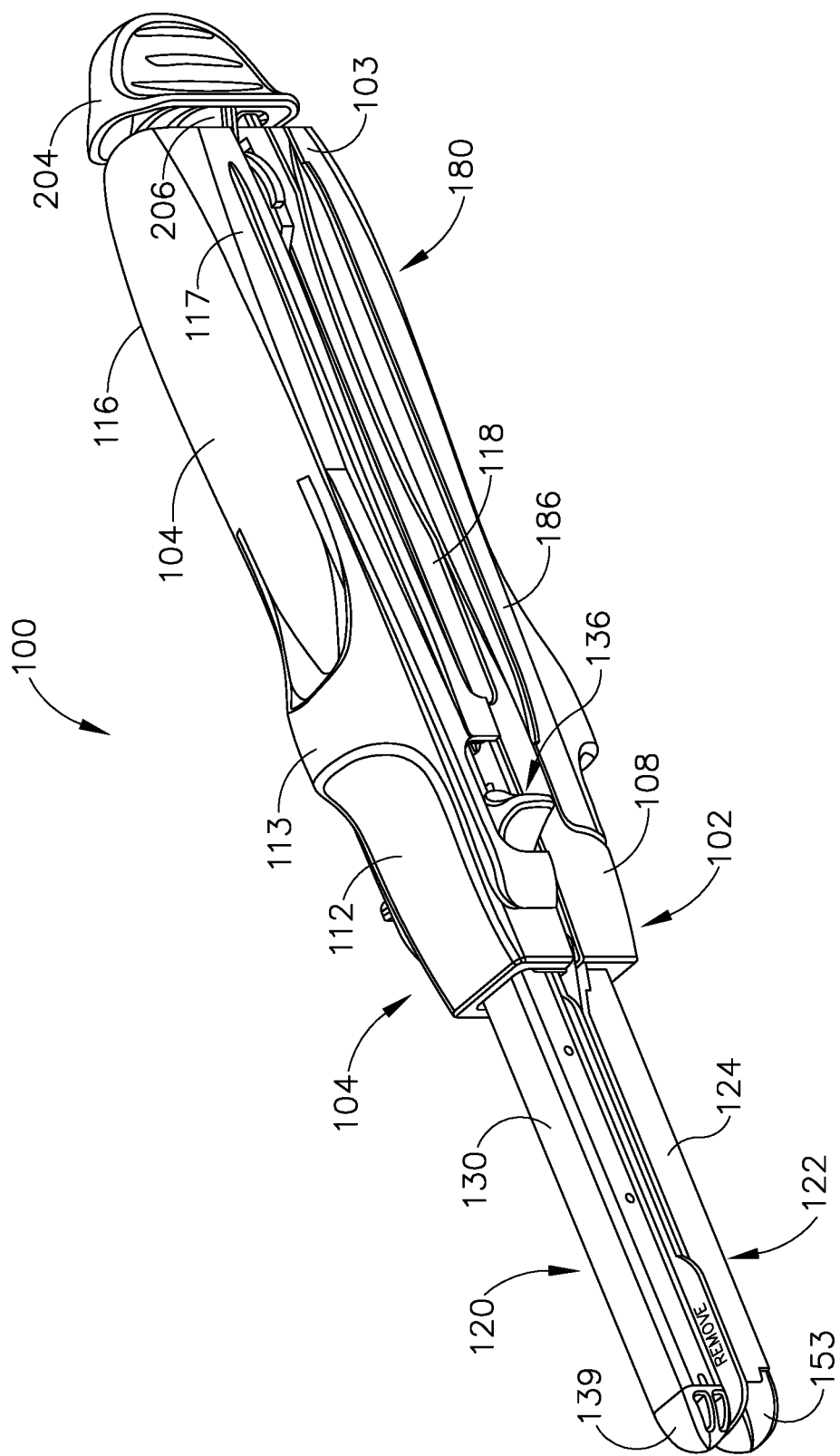
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. Exemplary Linear Cutting Stapler

A. Overview of Features of Linear Cutting Stapler

FIG. 1 depicts an exemplary surgical linear cutting stapler (100) that may be used for any suitable procedure, such as a gastrointestinal anastomosis. Linear cutting stapler (100) includes a first portion (102) having a staple cartridge channel (122), a second portion (104) having an anvil channel (130), a staple cartridge assembly (150) that may selectively couple with cartridge channel (122) of first portion (102), and a firing assembly (200). As will be described in greater detail below, first portion (102) and staple cartridge assembly (150) may pivotably couple with second portion (104) to form an end effector (120) capable of clamping, severing, and stapling tissue captured between opposing halves of end effector (120).

As best seen in FIGS. 3-6, firing assembly (200) includes an actuating beam (202), a staple sled assembly (160) housed within staple cartridge assembly (150), an actuator (204) (also referred to as a "firing knob"), and a pivot arm (206). Actuating beam (202) extends from a distal end (201) to a proximal end (203). Actuating beam (202) is slidably housed within first portion (102). Pivot arm (206) connects actuator (204) with distal end (201) of actuating beam (202). Actuator (204) and pivot arm (206) may pivot from a proximal position (shown in FIG. 1) to either lateral side of actuating beam (202) (shown in FIG. 11A), thereby enabling an operator to actuate firing assembly (200) from either a first side (116) or a second side (117) of instrument (100) when portions (102, 104) are properly coupled and end effector (120) is in the fully closed position. It should be understood when instrument (100) is properly coupled and end effector (120) is in the fully closed position, first portion (102) and second portion (104) define a slot (118) dimensioned to accommodate translation of actuator (204). In the current example, as will be described in greater detail below, actuating beam (202) is operable to couple with staple sled assembly (160) when staple cartridge assembly (150) is suitably coupled with first portion (102) such that actuator (204) may slide along first side (116) or second side (117) of instrument (100), thereby driving actuating beam (202) and staple sled assembly (160) distally through cartridge assembly (150) to fire instrument (100).

While in the present example, actuator (204) is configured to pivot to either side (116, 117) of instrument (100) to drive actuating beam (202), this is merely optional, as actuator (204) may slidably couple with first portion (102) or second portion (104) through any means apparent to one having ordinary skill in the art in view of the teachings herein. In one example, actuator (204) may strictly associate with first side (116) or second side (117) such that actuator (204) may not pivot when end effector (120) is in the fully closed position. In another example, there may be an actuator (204) positioned on both first side (116) and second side (117), such that instrument (100) may include two actuators (204).

Figure 3:
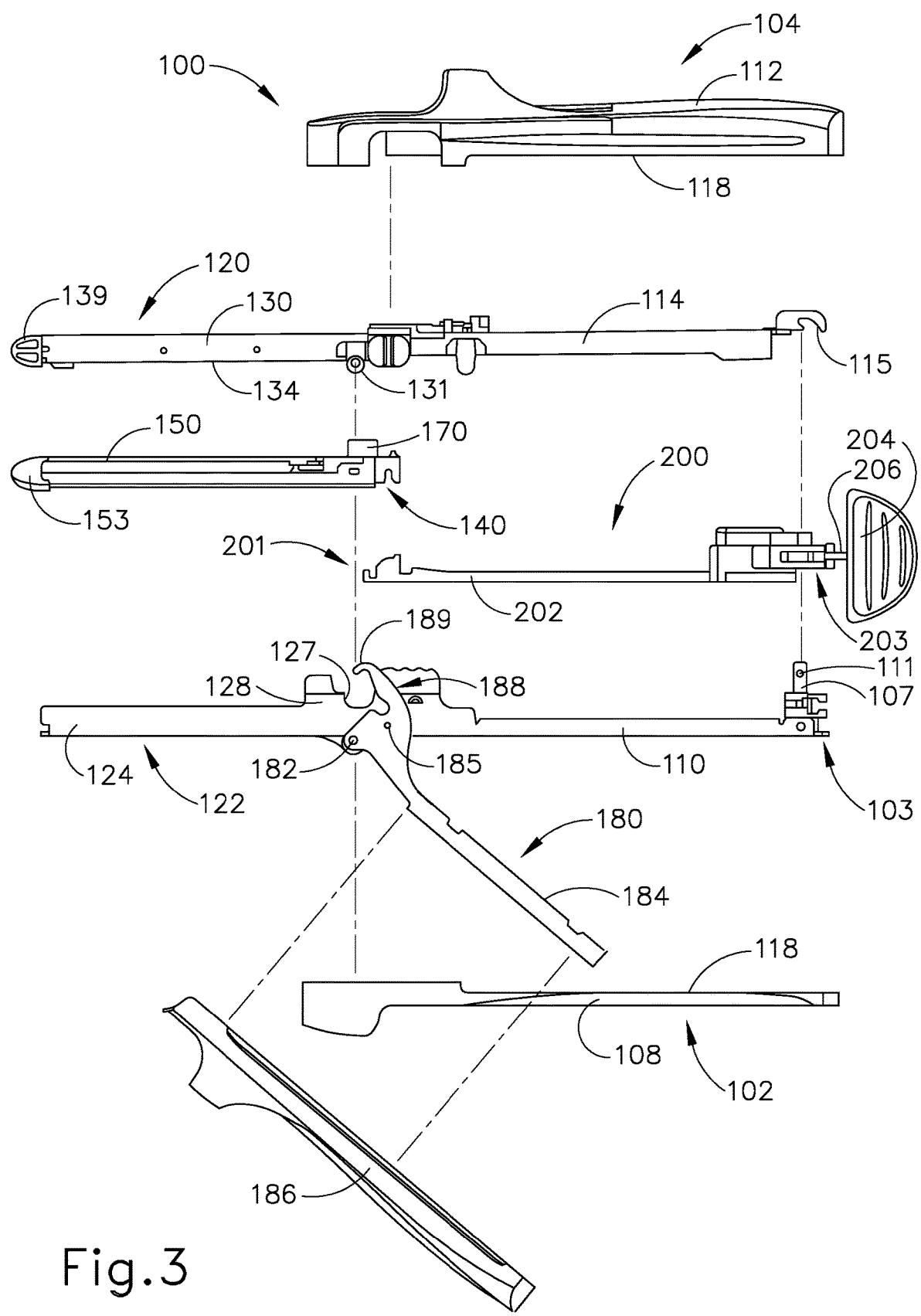
FIG. 3 depicts an exploded elevational side view of the surgical stapling instrument of FIG. 1.

As seen in FIG. 3, first portion (102) includes a first proximal frame (110), staple cartridge channel (122), and a closure lever in the form of latching lever (180). First proximal frame (110) extends from a proximal end (103) distally into staple cartridge channel (122). In the present example, first proximal frame (110) and staple cartridge channel (122) are formed integrally so as to define an elongate cartridge channel member having a unitary construction. Latching lever (180) is pivotably coupled to either staple cartridge channel (122) or first proximal frame (110) via a pin (182). First proximal frame (110) may be coupled with a handle cover (108) configured to promote sufficient grip such that an operator may control instrument (100) while the operator performs a suitable procedure. Handle cover (108) may couple with first proximal frame (110) by any suitable means as would be apparent to one having ordinary skill in the art in view of the teachings herein. Alternatively, handle cover (108) may be unitarily coupled with first proximal frame (110) or even omitted.

First proximal frame (110) defines a channel that slidably houses actuating beam (202) of firing assembly (200). Proximal end (103) includes one or more lateral pins, or projections (111). Projections (111) are configured to receive grooves (115) of second portion (104) in order to initially pivotably couple first and second portions (102, 104). In the current example, projections (111) are raised from the rest of first proximal frame (110) via a post (107), however this is merely optional. For instance, projections (111) may include a single pin extending laterally across side walls of first proximal frame (110). Of course, any suitable means of initially pivotably couplings first portion (102) and second portion (104) may be used as would be apparent to one having ordinary skill in the art in view of the teachings herein.

Figure 2:
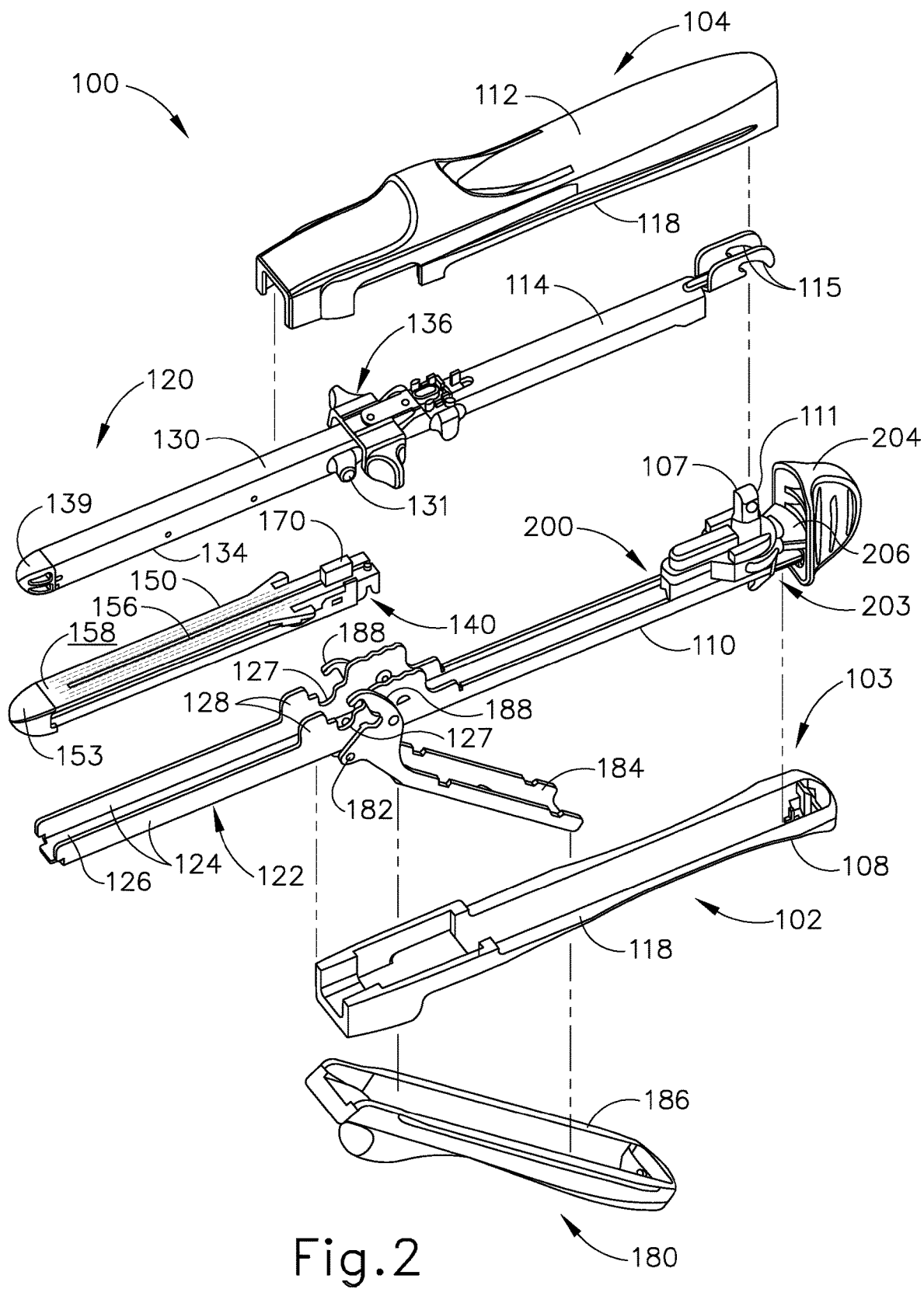
FIG. 2 depicts an exploded perspective view of the surgical stapling instrument of FIG. 1.
Figure 4:
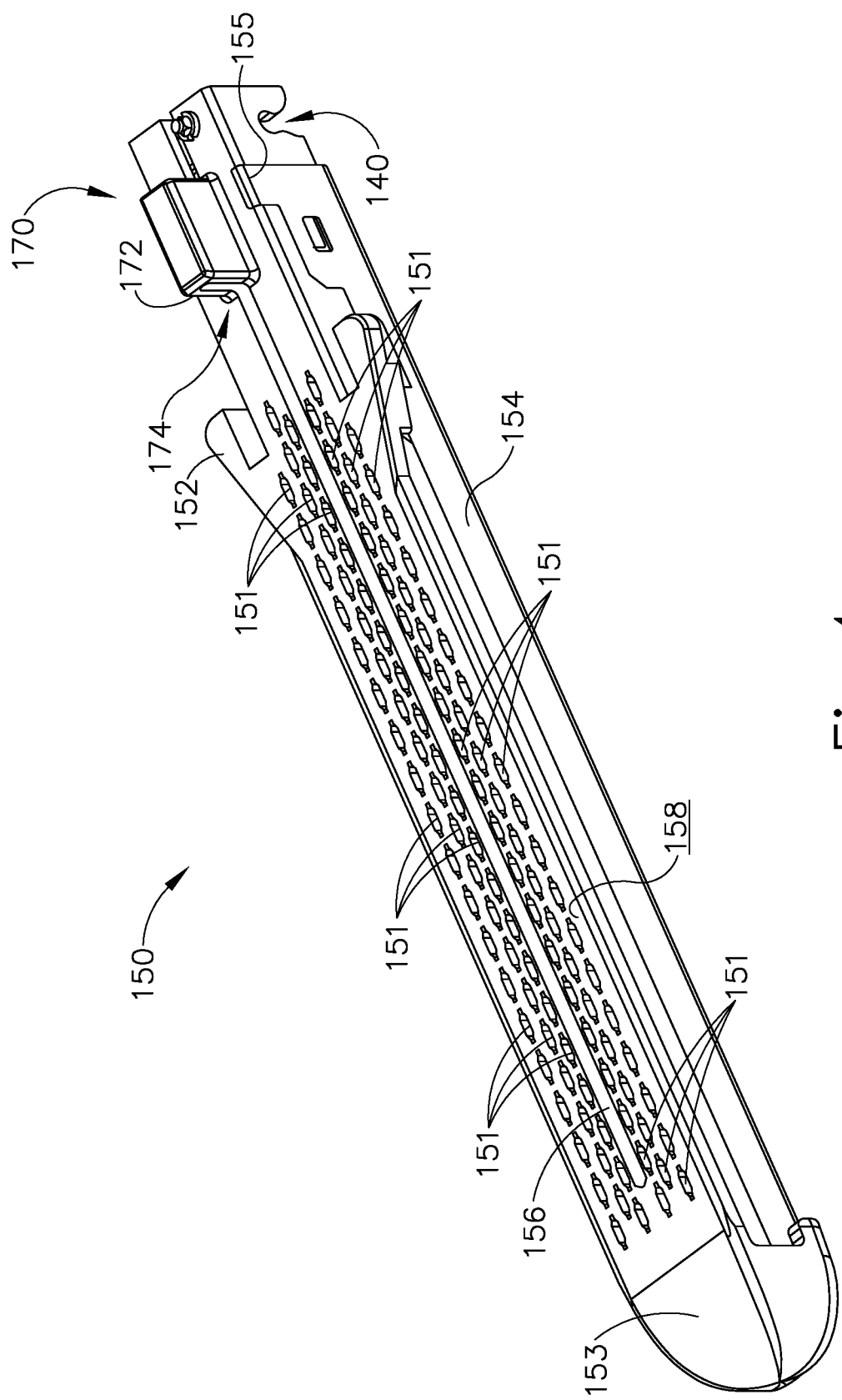
FIG. 4 depicts a perspective view of a staple cartridge assembly of the surgical stapling instrument of FIG. 1.

As briefly mentioned above, staple cartridge channel (122) extends distally from first proximal frame (110). As seen in FIG. 2, staple cartridge channel (122) is dimensioned to selectively couple and decouple with staple cartridge assembly (150). Staple cartridge channel (122) includes a bottom wall (126), and two opposed side walls (124) extending from opposite ends of bottom wall (126). Walls (124, 126) are dimensioned to receive at least a portion of staple cartridge assembly (150), as seen in FIG. 4. Additionally, side walls (124) include inwardly extending lateral projections (not shown) configured to receive coupling cutouts (140) defined by a proximal end of staple cartridge assembly (150). Coupling cutouts (140) may be dimensioned for a snap-fitting or press-fitting with inwardly extending lateral projections (not shown) of side walls (124) such that an operator may selectively attach and detach staple cartridge assembly (150) to staple cartridge channel (122). While coupling cutouts (140) and inwardly extending lateral projections (not shown) are used to selectively couple staple cartridge assembly (150) with staple cartridge channel (122), any other suitable coupling means may be used as would be apparent to one having ordinary skill in the art in view of the teachings herein. Side walls (124) of staple cartridge channel (122) also include side flanges (128) each defining a notch or recess (127). Recesses (127) are dimensioned to receive latch projections (131) of second portion (104) when second portion (104) pivots such that end effector (120) is in a fully closed position (as shown in FIG. 10D) relative to first portion (102).

As briefly mentioned above, latching lever (180) is pivotably coupled to the rest of first portion (102) via pivot pin (182). Latching lever (180) includes a proximal extending arm (184) and a distal latch body (188). Proximal extending arm (184) may be pivoted about pin (182) toward first proximal frame (110) in order to pivot distal latch body (188) toward staple cartridge channel (122) such that distal latch body (188) may engage and pivot second portion (104) toward first portion (102) to transition end effector (120) from a partially closed position (as shown in FIG. 10C) to a fully closed position (as shown in FIG. 10D).

Proximally extending arm (184) may be coupled with an arm cover (186) to promote sufficient grip such that an operator may grasp arm (184) while the operator performs a suitable procedure. Arm cover (186) may be coupled with proximal extending arm (184) by any suitable means as would be apparent to one having ordinary skill in the art in view of the teachings herein. Alternatively, arm cover (186) may be unitarily coupled with proximally extending arm (184) or even omitted.

Distal latch body (188) includes a pair of hooks (189) (or "jaws"). Distal latch body (188) also defines a corresponding pair of latch cutouts (185) located proximally relative to hooks (189). As will be described is greater detail below, each hook (189) is dimensioned to initially make contact with and then capture a respective latch projection (131) of second portion (104) such that distal latch body (188) may wrap around at least a portion of each latch projection (131) to further pivot second portion (104) toward first portion (102). As will also be described in greater detail below, each latch cutout (185) is dimensioned to receive a respective latch projection (131) when end effector (120) is in the closed position relative to first portion (102).

Figure 5:
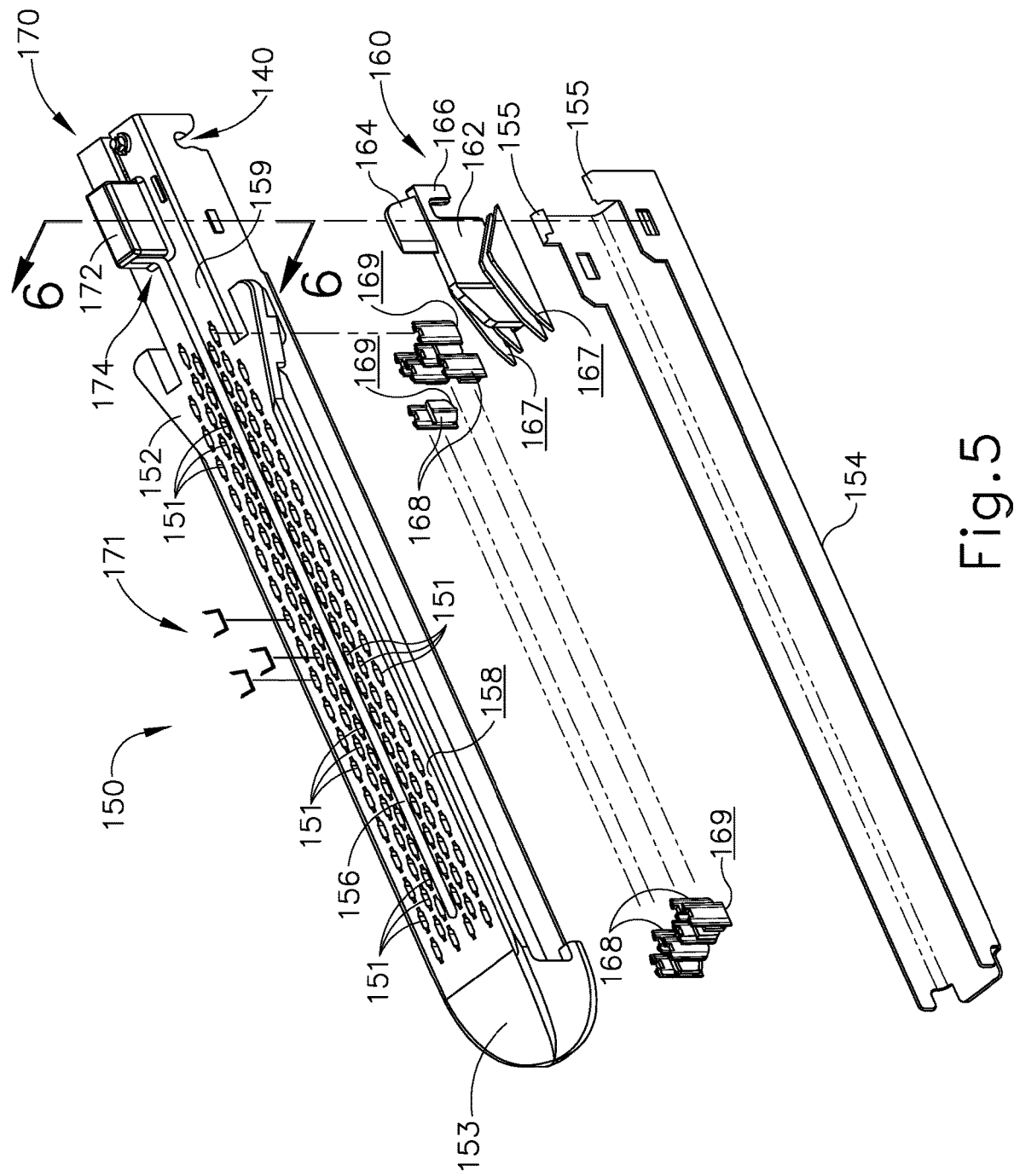
FIG. 5 depicts an exploded view of the staple cartridge assembly of FIG. 4.
Figure 6:
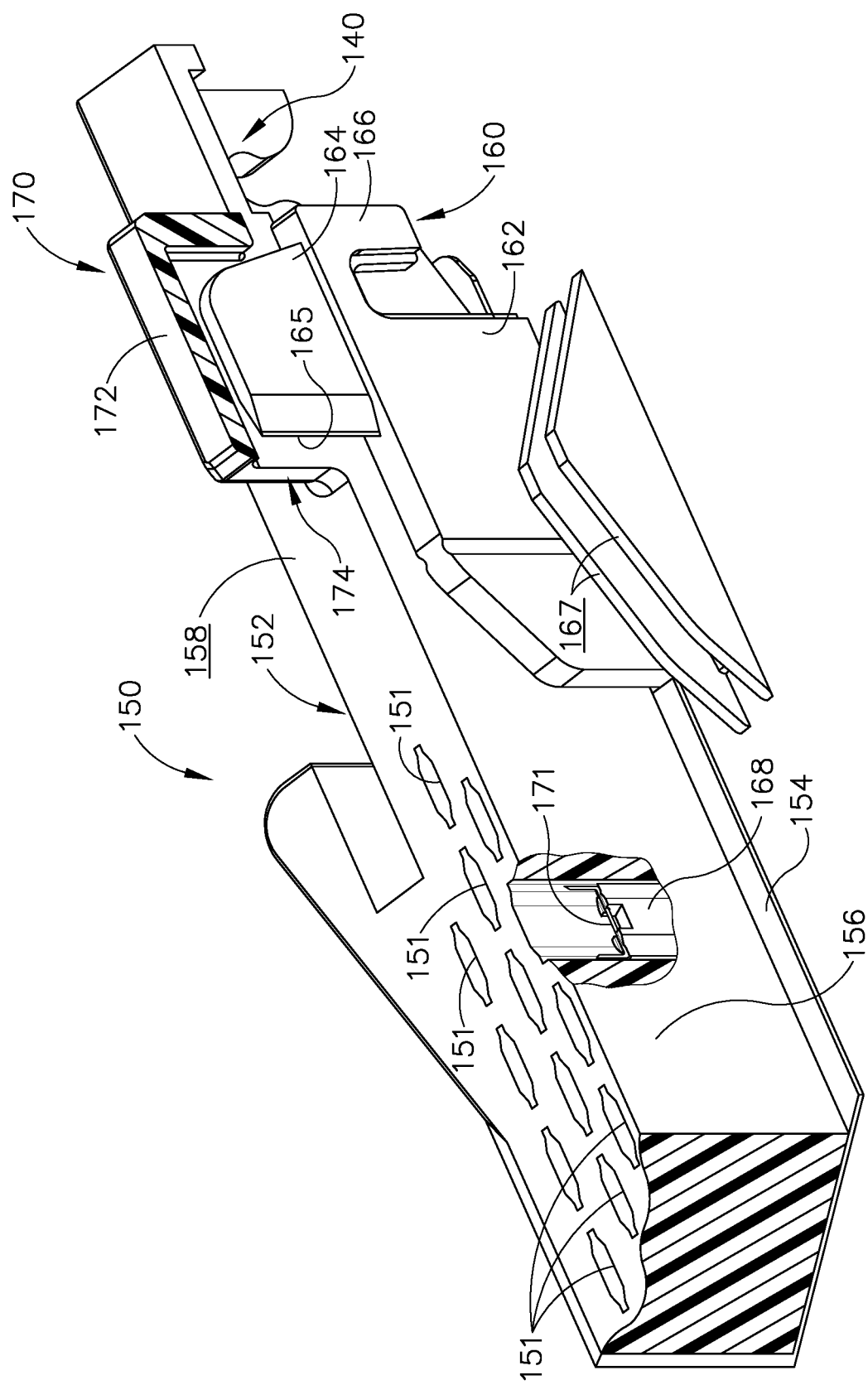
FIG. 6 depicts a cross-sectional perspective view of the staple cartridge assembly of FIG. 4, taken along line 6-6 of FIG. 5.

As best seen in FIGS. 4-6, staple cartridge assembly (150) includes a cartridge body (152), a pan (154), and a plurality of staple drivers (168), each configured to drive a respective staple (171). Cartridge body (152) defines a plurality of staple cavities (151), a slot (156), and coupling cutouts (140). Staple drivers (168) and respective staples (171) are slidably housed within a corresponding staple cavity (151). When first portion (102) and second portion (104) are coupled together, staple cartridge assembly (150) and staple cartridge channel (122) form a portion of end effector (120). As will be described in greater detail below, staple cartridge assembly (150) is configured to house or receive staple sled assembly (160) of firing assembly (200) such that staple sled assembly (160) may actuate through cartridge assembly (150) in order to simultaneously sever and staple tissue captured between the two halves of end effector (120).

As mentioned above, coupling cutouts (140) of cartridge body (152) may be dimensioned for a snap-fitting with inwardly extending lateral projections (not shown) of side walls (124) of staple cartridge channel (122) such that an operator may selectively attach and detach staple cartridge assembly (150) to staple cartridge channel (122). Cartridge body (152) includes a distal nose (153). When staple cartridge assembly (150) is properly coupled with cartridge channel (122), distal nose (153) may extend distally from cartridge channel (122) to provide an atraumatic tip.

Additionally, cartridge body (152) includes a staple deck (158). Staple deck (158) partially defines staple cavities (151) such that staple cavities (151) extend from an interior of cartridge body (152) toward an open end at staple deck (158). Staple cavities (151) each house a corresponding staple driver (168) and staple (171). Similarly, staple deck (158) partially defines slot (156) that extends from an interior of cartridge body (152) toward an open end at staple deck (158). Slot (156) is dimensioned to slidably receive a portion of a sled body (162) and cutting member (164) of staple sled assembly (160) such that cutting member (164) may sever tissue as staple sled assembly (160) slides distally through cartridge body (152).

Pan (154) may include flexible arms (155). Flexible arms (155) may be configured to engage cartridge body (152) such that pan (154) may couple with cartridge body (152) in a snap-fit or press-fit relationship. Pan (154) may couple with cartridge body (152) after staple drivers (168) and staples (171) have been inserted into respective staple cavities (151). Pan (154) may therefore act as a floor for staple drivers (168).

In the current example, cartridge body (152) includes a sled assembly housing (170) located near the proximal end of staple cartridge assembly (150). Sled assembly housing (170) is configured to initially house staple sled assembly (160) of firing assembly (200). Sled assembly housing (170) includes a body (172) defining a cavity (174) having a distally facing opening. Body (172) and cavity (174) are dimensioned to house a cutting member (164) of sled assembly (160) prior to firing, therefore acting as a sheath for cutting member (164). When fired, cutting member (164) may exit sled assembly housing (170) via the distally facing opening of cavity (174).

As seen best in FIGS. 7 and 8, sled assembly (160) includes a sled body (162) and a cutting member (164). Cutting member (164) includes a cutting edge (165) and a lock arm (166). Sled body (162) defines a cutout (161) and a slot (163). Slot (163) is dimensioned to receive a portion of cutting member (164) such that cutting member (164) and sled body (162) may actuate together. Cutting member (164) may couple with sled body (162) via an inference fit with slot (163), through use of adhesives, or any other suitable manner was would be apparent to one having ordinary skill in the art in view of the teachings herein. Alternatively, cutting member (164) may couple with sled body (162) though any suitable manner as would be apparent to one having ordinary skill in the art in view of the teachings herein, such as being unitarily connected, welding, etc. Cutout (161) is dimensioned to couple with distal end (201) of actuating beam (202) when staple cartridge assembly (150) is properly attached to staple cartridge channel (122). Therefore, when properly coupled, actuating beam (202) may drive sled assembly (160) longitudinally through cartridge body (152). It should be understood that since actuating beam (202) is coupled with sled assembly (160) during exemplary use, actuating beam (202) is also dimensioned to slide within slot (156) defined by cartridge body (152).

Sled body (162) also includes a plurality of cam surfaces (167) dimensioned to slide longitudinally within respective elongate grooves (not shown) that pass through staple cavities (151) of cartridge body (152). In particular, cam surface (167) are configured to engage and cam against sloped surfaces (169) of staple drivers (168) within staple cavities (151) in order to actuate staple drivers (168) toward staple deck (158). Staple drivers (168) then drive corresponding staples (171) through staple cavities (151) away from staple deck (158).

As mentioned above, staple sled assembly (160) is configured to couple with the rest of firing assembly (200) when staple cartridge assembly (150) is suitably coupled with staple cartridge channel (122). In the current example, staple sled assembly (160) of firing assembly (200) is associated with cartridge assembly (150) such that after cartridge assembly (150) is used and disposed of, so is staple sled assembly (160). Therefore, when an additional cartridge assembly (150) is loaded into staple cartridge channel (122), a new staple sled assembly (160) will be present. However, this is merely optional. For instance, staple sled assembly (160) may be fixed or otherwise coupled to the rest of firing assembly (200) such that the same staple sled assembly (160) may be used multiple times with multiple staple cartridge assemblies (150). In such examples, cartridge body (152) would not need a sled assembly housing (170). Various ways in which staple sled assembly (160) may be incorporated into either staple cartridge assembly (150), staple cartridge channel (122), or first proximal frame (110) will be apparent to one having ordinary skill in the art in view of the teachings herein.

As shown in FIGS. 2 and 3, second portion (104) of instrument (100) includes a second proximal frame (114), anvil channel (130), latch projections (131), and an anvil surface disposed along and supported by anvil channel (130) and shown in the form of anvil plate (134). Second proximal frame (114) extends from a proximal end defining grooves (115) in anvil channel (130). In the present example, second proximal frame (114) and anvil channel (130) are formed integrally so as to define an elongate anvil channel member having a unitary construction. Second proximal frame (114) may be coupled with a handle cover (112) configured to promote sufficient grip such that an operator may control instrument (100) while the operator performs a suitable procedure. Handle cover (112) and second proximal frame (114) may couple with each other by any suitable means as would be apparent to one having ordinary skill in the art in view of the teachings herein. Alternatively, handle cover (112) may be unitarily coupled with second proximal frame (114) or even omitted. Second proximal frame (114) may also define a channel configured to enable portions of firing assembly (200) to actuate relative to first portion (102) and second portion (104) when end effector (120) is in the fully closed position (as shown in FIG. 10D).

Figure 9:
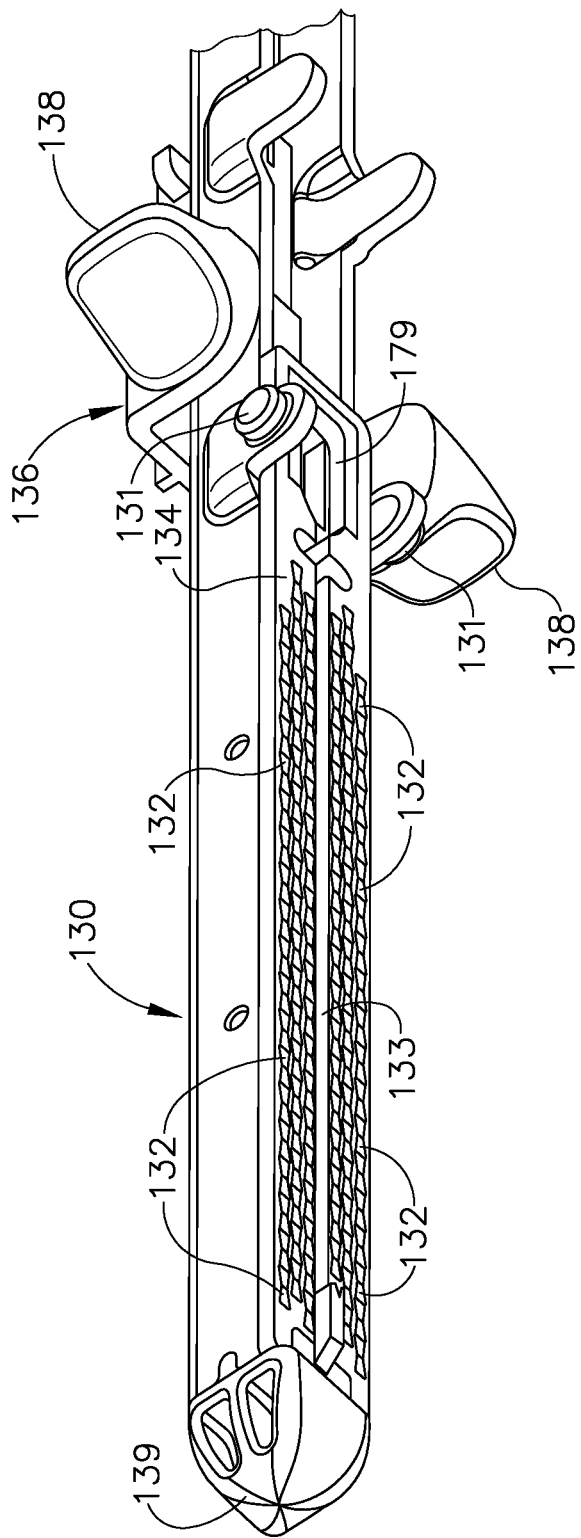
FIG. 9 depicts a perspective view of an anvil assembly of the surgical stapling instrument of FIG. 1.

Second portion (104) terminates distally in a distal nose (139). Distal nose (153) may extend distally from anvil channel (130) to provide an atraumatic tip. As shown in FIG. 9, proximal end of anvil plate (134) defines a recess (179) dimensioned to receive sled assembly housing (170) when first portion (102) and second portion (104) are pivoted toward each other. As will be described in greater detail below, latch projections (131) extend laterally away from anvil channel (130) and are dimensioned to interact with distal latch body (180) to draw anvil plate (134) toward staple cartridge assembly (150).

Anvil plate (134) defines a plurality of staple forming pockets (132) and a slot (133). Staple forming pockets (132) are positioned along anvil plate (134) such that each staple forming pocket (132) aligns with a corresponding staple cavity (151) when anvil channel (130) is pivoted toward staple cartridge channel (122) to the fully closed position (as shown in FIGS. 1, 10D, and 11A-B). Therefore, when cam surfaces (167) of sled body (162) actuate staple drivers (168) in accordance with the description above, staples (171) are driven through staple cavities (151) away from staple deck (158), through tissue, and against a corresponding staple forming pocket (132) such that staples (171) transform from a general "U" shape into a general "B" shape in order to suitably staple tissue. Slot (133) is dimensioned to laterally align with slot (156) of staple cartridge assembly (150) when anvil channel (130) is pivoted to the fully closed position (as shown in FIGS. 1, 10D, 11A-11B). Slot (133) is dimensioned to slidably receive a portion of cutting member (164) as staple sled assembly (160) is driven through staple cartridge assembly (150) such that cutting member (164) may sever tissue captured between anvil surface (134) and staple deck (158) during exemplary use.

As seen best in FIG. 9, second portion (104) of instrument (100) of the present example further includes a staple height adjustment mechanism (136). Adjustment mechanism (136) is operatively coupled with anvil plate (134), for example via one or more camming features (not shown), and includes a pair of user-engageable projections (138). Adjustment mechanism (136) is selectively movable relative to anvil channel (130) between two or more longitudinal positions to raise or lower anvil plate (134) relative to anvil channel (130), and thereby adjust a gap distance (or "tissue gap") between anvil plate (134) and staple deck (158) when first and second instrument portions (102, 104) are coupled together in a fully closed position. A larger gap distance, and thus a greater staple height, may be provided for stapling tissues of greater thicknesses. Similarly, a smaller gap distance, and thus a smaller staple height, may be provided for stapling tissues of lesser thicknesses. It will be appreciated that staple height adjustment mechanism (136) is merely optional and may be omitted in other versions. In some versions of instrument (100), the anvil surface, shown in the form of anvil plate (134), may be fixed relative to anvil channel (130). For instance, the anvil surface may be formed integrally with anvil channel (130).

Surgical linear cutting stapler (100) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Cutting Stapler

Figure 10A:
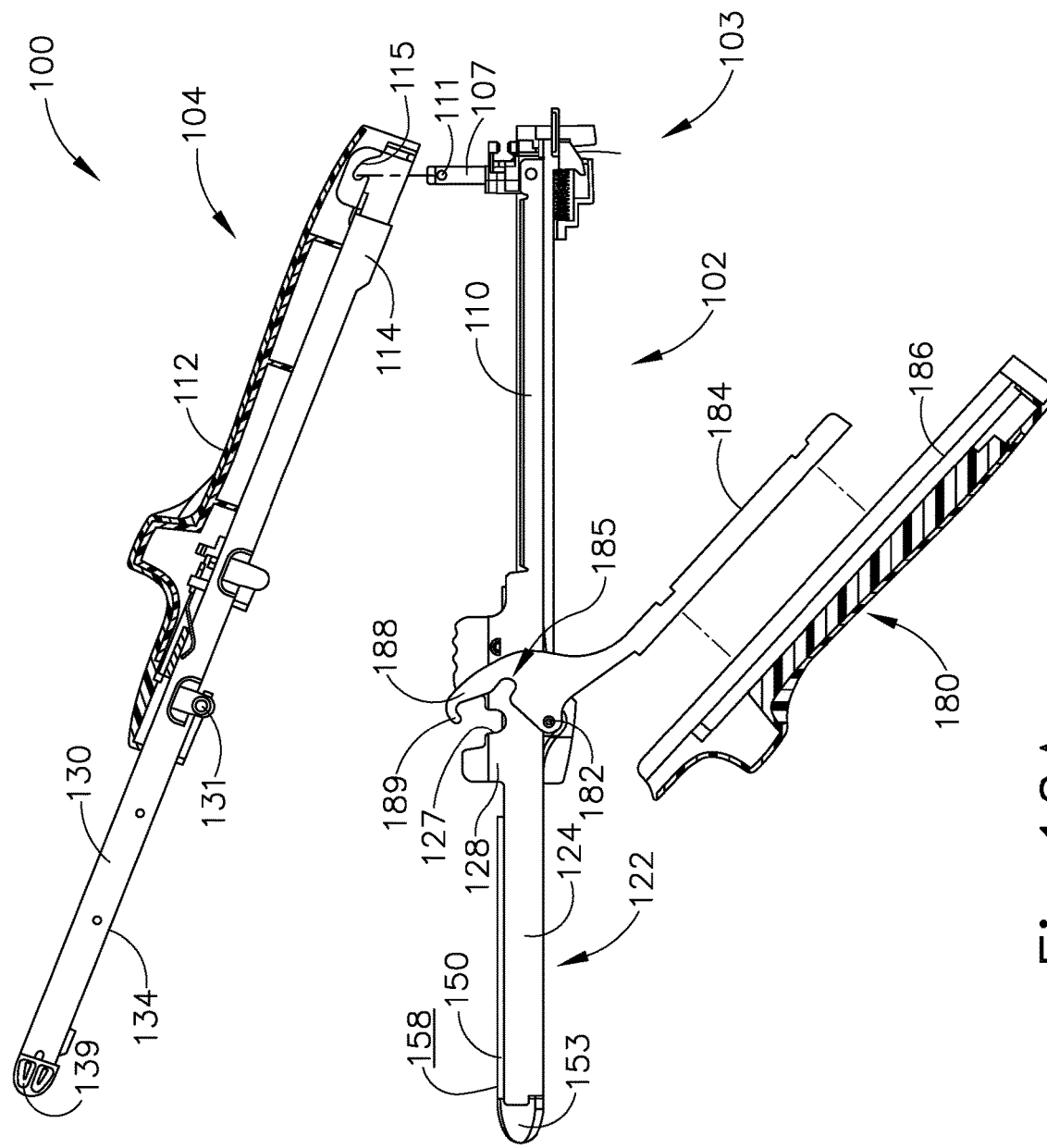
FIG. 10A depicts a cross-sectional side view of the surgical stapling instrument of FIG. 1, where a first portion and a second portion are decoupled from each other, and where an arm cover of the second portion is shown detached from the first portion for illustrative purposes.
Figure 10B:
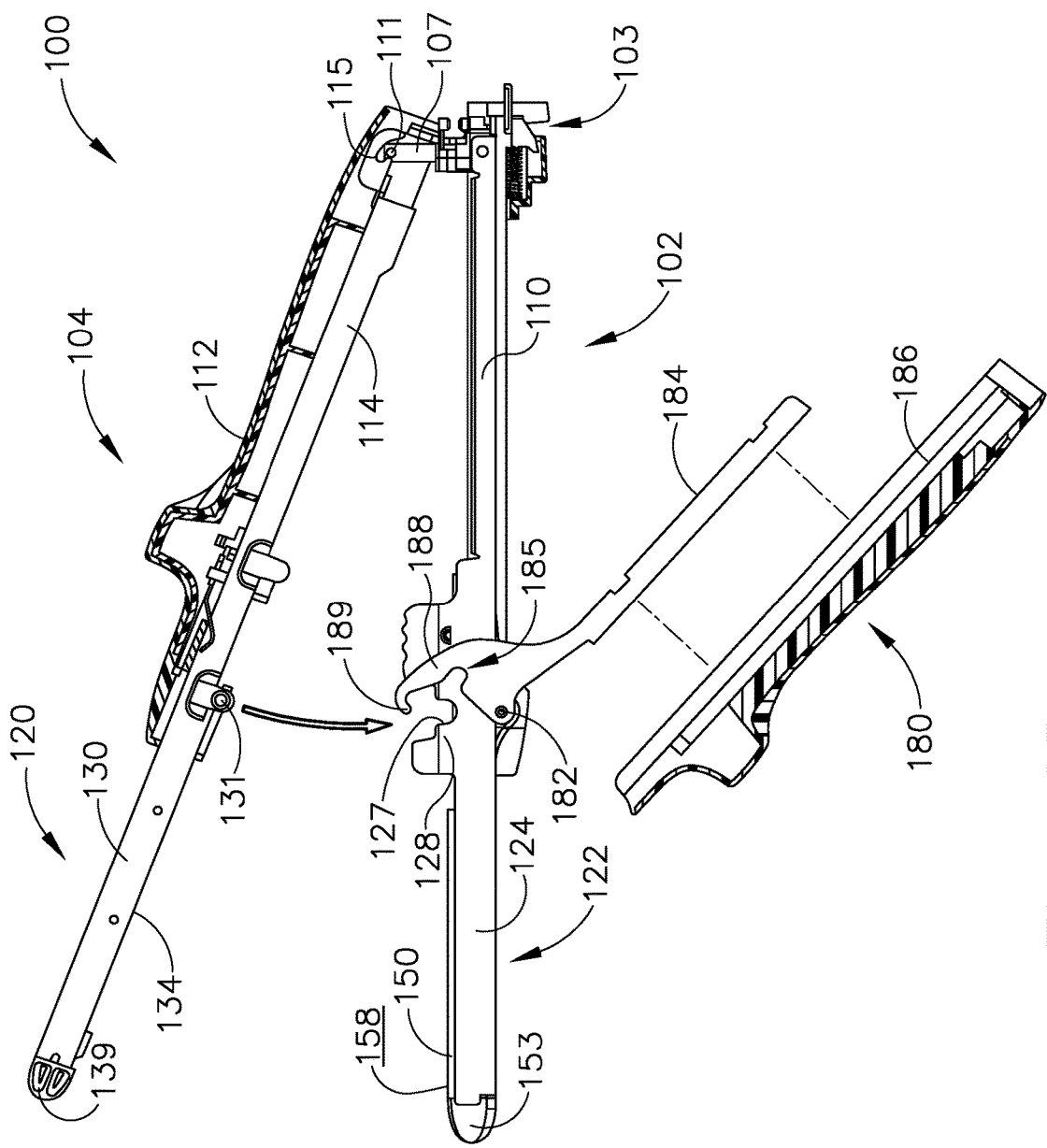
FIG. 10B depicts a cross-sectional side view of the surgical instrument of FIG. 1, where the first portion and the second portion of FIG. 10A are coupled with each other in an opened position.
Figure 10C:
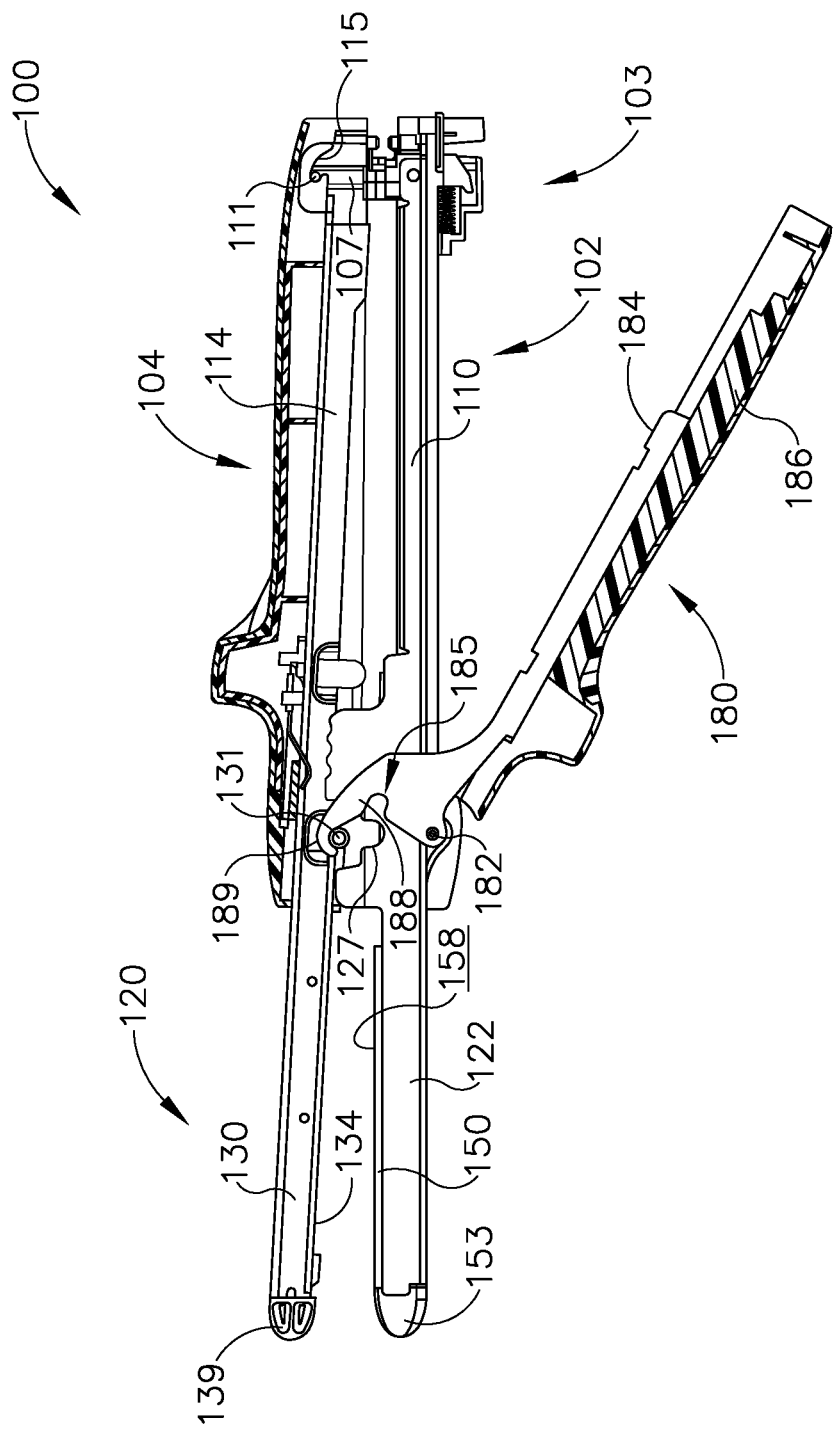
FIG. 10C depicts a cross-sectional side view of the surgical instrument of FIG. 1, where the first portion and the second portion of FIG. 10A are coupled with each other in a partially closed position.
Figure 10D:
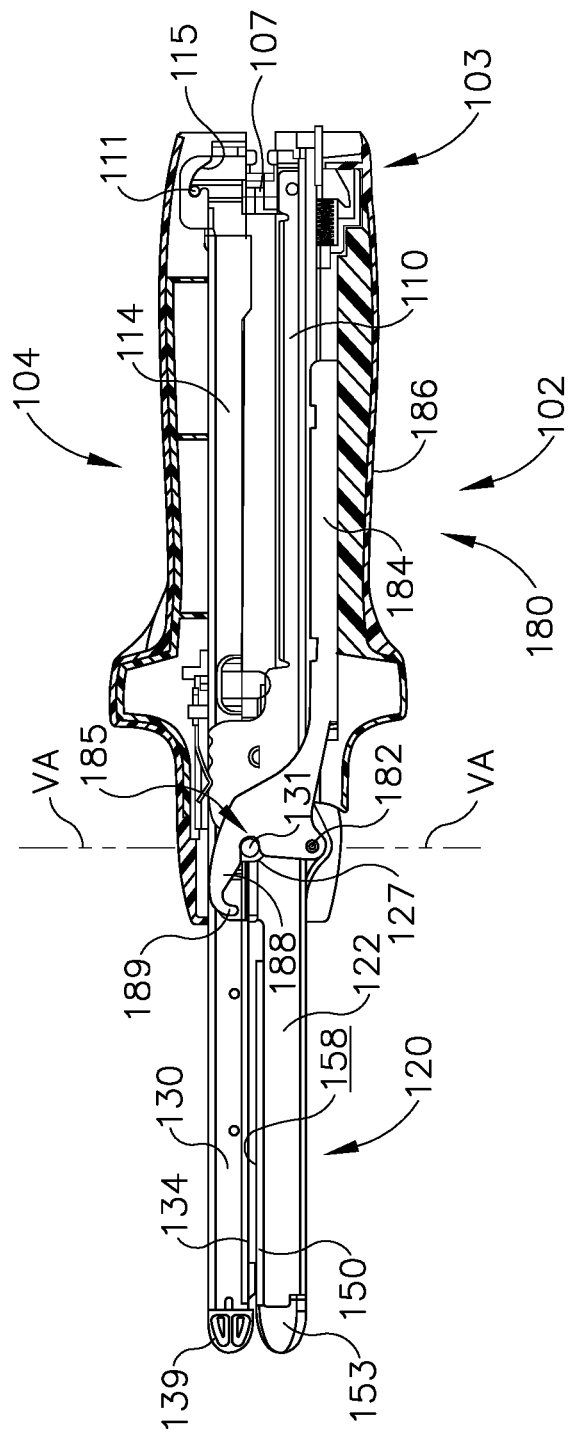
FIG. 10D depicts a cross-sectional side view of the surgical instrument of FIG. 1, where the first portion and the second portion of FIG. 10A are coupled with each other in a fully closed position.
Figure 11A:
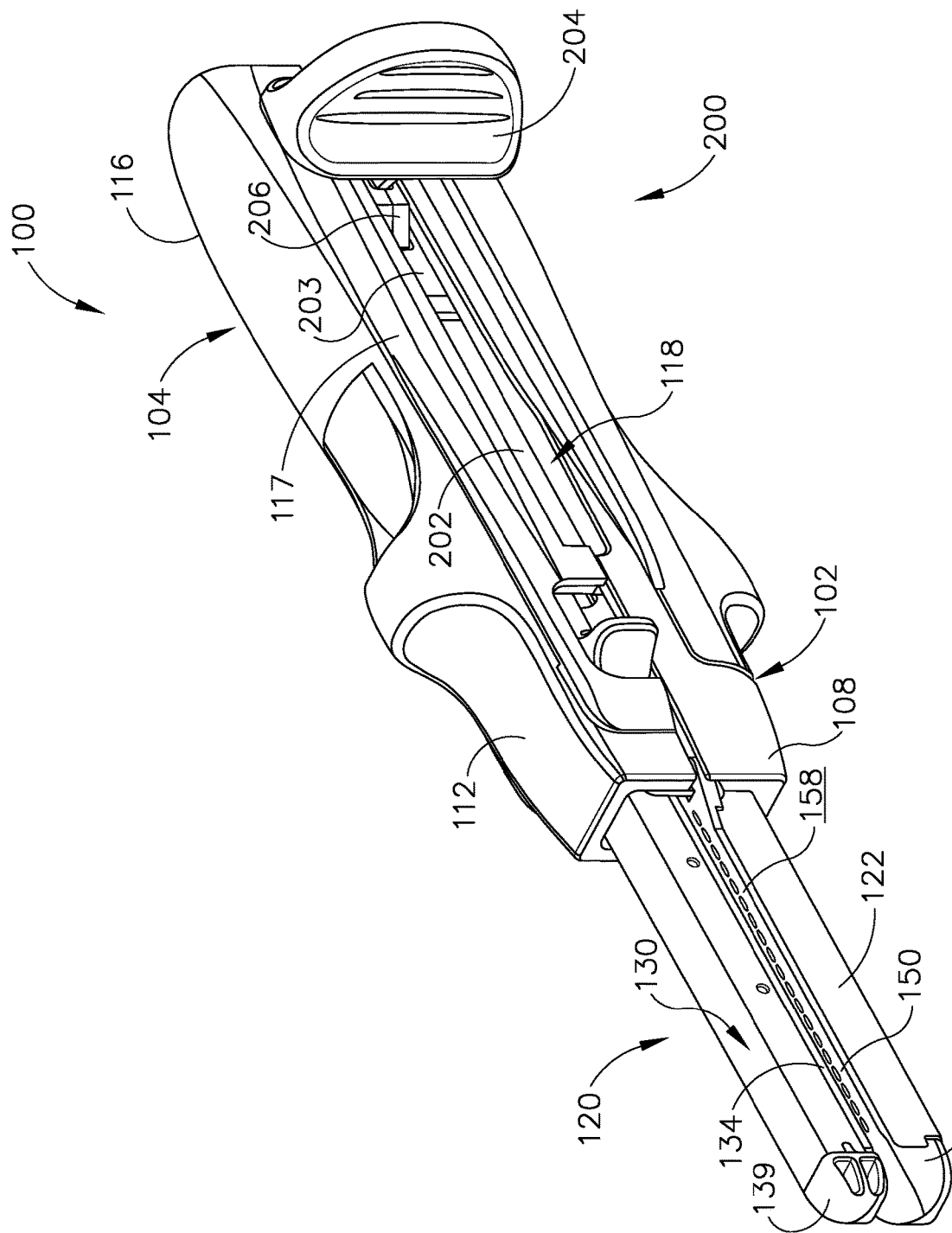
FIG. 11A depicts a perspective view of the surgical instrument of FIG. 1, where a firing assembly is in a pre-fired position.
Figure 11B:
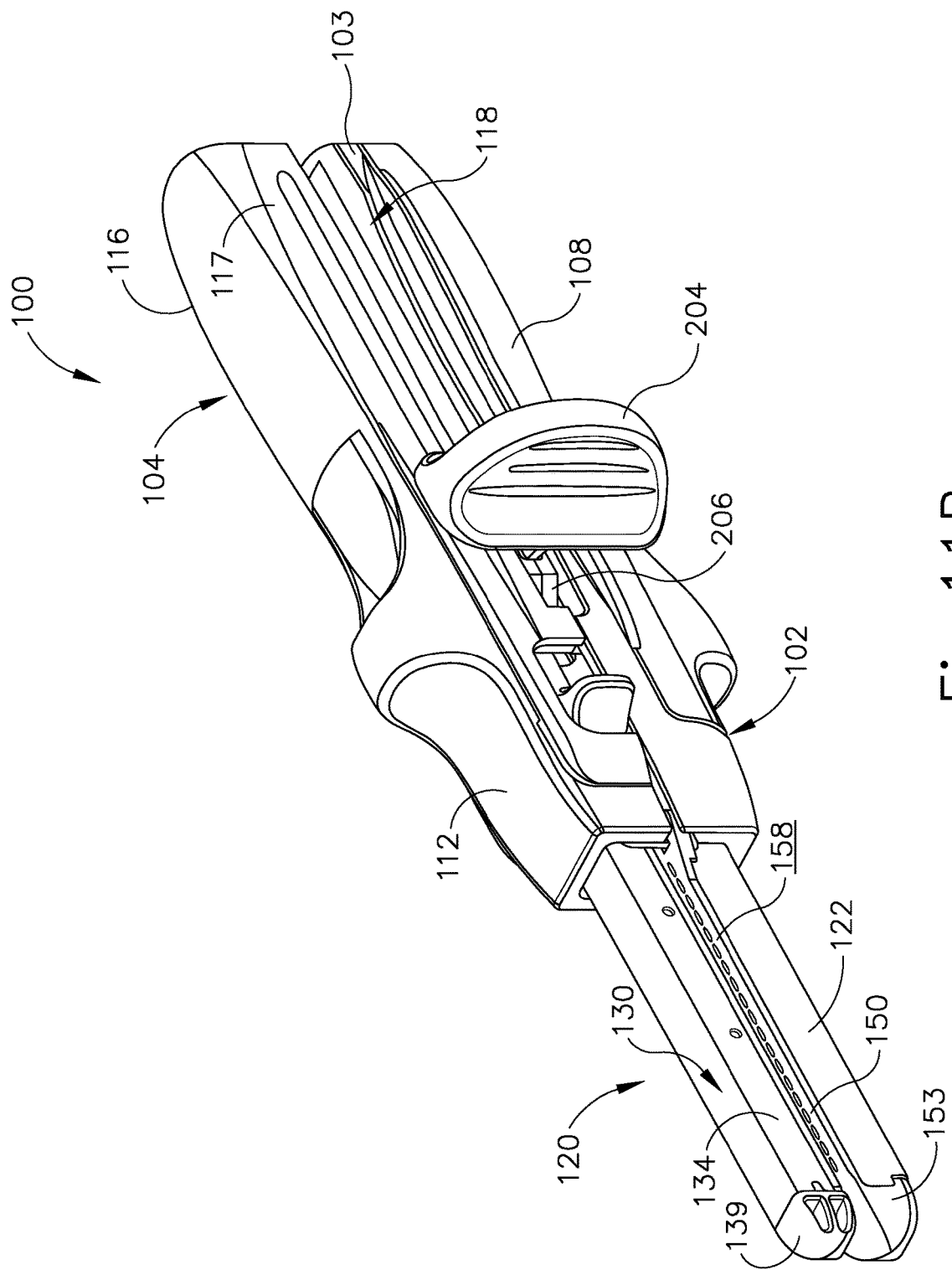
FIG. 11B depicts a perspective view of the surgical instrument of FIG. 1, where the firing assembly of FIG. 11A is in a fired position.

FIGS. 10A-11B show an exemplary use of linear cutting stapler (100). In particular, FIGS. 10A-10D show an exemplary coupling of first portion (102) with second portion (104), and pivoting first portion (102) and second portion (104) such that end effector (120) transitions from an open position (FIG. 10B), to a partially closed position (FIG. 10C), and finally to a fully closed position (FIG. 10D). FIGS. 11A-11B show an exemplary firing of instrument (100) when end effector (120) is in a fully closed position.

FIG. 10A shows first portion (102) completely detached from second portion (204). Additionally, staple cartridge assembly (150) is suitably attached to staple cartridge channel (122) in accordance with the description above. At this point during a procedure, such as during a gastrointestinal anastomosis, an operator may desire to place lumens of tissue over and past distal noses (139, 153) of second portion (104) and cartridge assembly (150), respectively, such that lumens of tissue are suitably associated with both anvil plate (134) and cartridge assembly (150). At this point, an operator may align grooves (115) of second portion (104) with corresponding lateral projections (111) of first portion (102) in preparation of initially pivotally coupling first portion (102) with second portion (104).

Next, as shown in FIG. 10B, an operator may insert lateral projections (111) into corresponding grooves (115) such that first portion (102) and second portion (104) are pivotally coupled, but end effector (120) is in an open position. First portion (102) and second portion (104) may pivot relative to each other about the axis defined by lateral projections (111). At this point, latching lever (180) is not in contact with any portion of second portion (104). Additionally, latching lever (180) is in an open position such that proximal extending arm (184) is pivoted away from first proximal frame (110).

Next, as shown in FIG. 10C, an operator may initially pivot anvil channel (130) and anvil plate (134) toward cartridge channel (122) and staple cartridge assembly (150), and partially pivot latching lever (180) such that hooks (189) initially contact latch projections (131). At this point, end effector (120) is in the partially closed position. As best shown between FIGS. 10C-10D, after hooks (189) initially contact latch projections (131), an operator may further rotate proximal extending arm (184) toward first proximal frame (110), causing distal latch body (188) to drive latch projections (131) along the surfaces of distal latch body (188) toward latch cutouts (185). As latch projections (131) are driven toward latch cutouts (185), anvil channel (130) and anvil plate (134) rotate further toward cartridge channel (122) and staple cartridge assembly (150) such that end effector (120) is in the closed position. Additionally, latch projections (131) are also driven toward recesses (127) of staple cartridge channel (122) such that each latch projection (131) is encompassed by a combination of the respective latch cutout (185) and recess (127), effectively latching end effector (120) into the closed position. Latch cutouts (185) and recesses (127) may be dimensioned to interface with latch projections (131) while end effector (120) is in the fully closed position such that latch projections (131) and pivot pin (182) extend along a vertical axis (VA) that is substantially perpendicular with the longitudinal axis of instrument (100). This may provide a mechanical advantage for an enhanced closure force during suitable use.

FIGS. 11A-11B show an exemplary firing of instrument (100) with end effector (120) in the fully closed position. As best seen in FIG. 11A, an operator may pivot actuator (204) to either side (116, 117) of instrument (100). In the present example, actuator (204) has been pivoted to second side (117) of instrument (100). Next, operator may push actuator (204) distally toward end effector (120) within slot (118), such that actuating beam (202) and sled (160) are fired, thereby stapling and severing tissue captured between stapling deck (158) and anvil plate (134) in accordance with the description above. Once instrument (100) has been fired, an operator may pull actuator (204) proximally back to the position shown in FIG. 11A, then rotate actuator (204) back to the position shown in FIG. 1. An operator may then pivot latching lever (180) such that proximally extending arm (184) is pivoted away from first proximal frame (110) in order to open end effector (120) from the fully closed position to the partially closed position. An operator may further pivot latching lever (180) such that distal latch body (188) no longer captures latch projections (131). Then an operator may decouple first portion (102) and second portion (104) from each other and replace staple cartridge assembly (150), if desired.

II. Exemplary Linear Cutting Stapler Having Latch Lockout Member

As described above, latching lever (180) of stapler (100) is movable between an open position (FIG. 10B) in which lever (180) permits stapler halves (102, 104) to be separated from one another, and a closed position in which lever (180) fixes stapler halves (102 104) to one another. Specifically, latching lever (180) of cartridge half (102) captures latch projections (131) of anvil half (104) when in the closed position to secure stapler halves (102, 104) together. Latching lever (180) should be maintained in the open position while stapler halves (102, 204) are initially brought together, to ensure that latch projections (131) can align properly with and be received by the capturing features of latching lever (180).

In some instances, it may be desirable to provide a linear cutting stapler with a feature that securely maintains the latching lever in the open position while the stapler halves are being assembled. Surgical stapler (300) described below includes such a feature in the form of latch lockout member (350). As described in greater detail below in connection with FIGS. 13A-13D, latch lockout member (350) is configured to actuate between a lever lockout state (FIG. 13A) and a lever release state (FIG. 13C) in response to anvil half (304) of stapler (300) being assembled with cartridge half (302). Advantageously, this configuration enables an operator to easily manipulate stapler halves (302, 304) relative to one another and relative to tissue being clamped without having to simultaneously expend effort on ensuring that latching lever (318) remains in the open position to enable proper alignment of lever (318) with a latch pin (346) of anvil half (304).

A. Overview of Exemplary Linear Cutting Stapler

Figure 12:
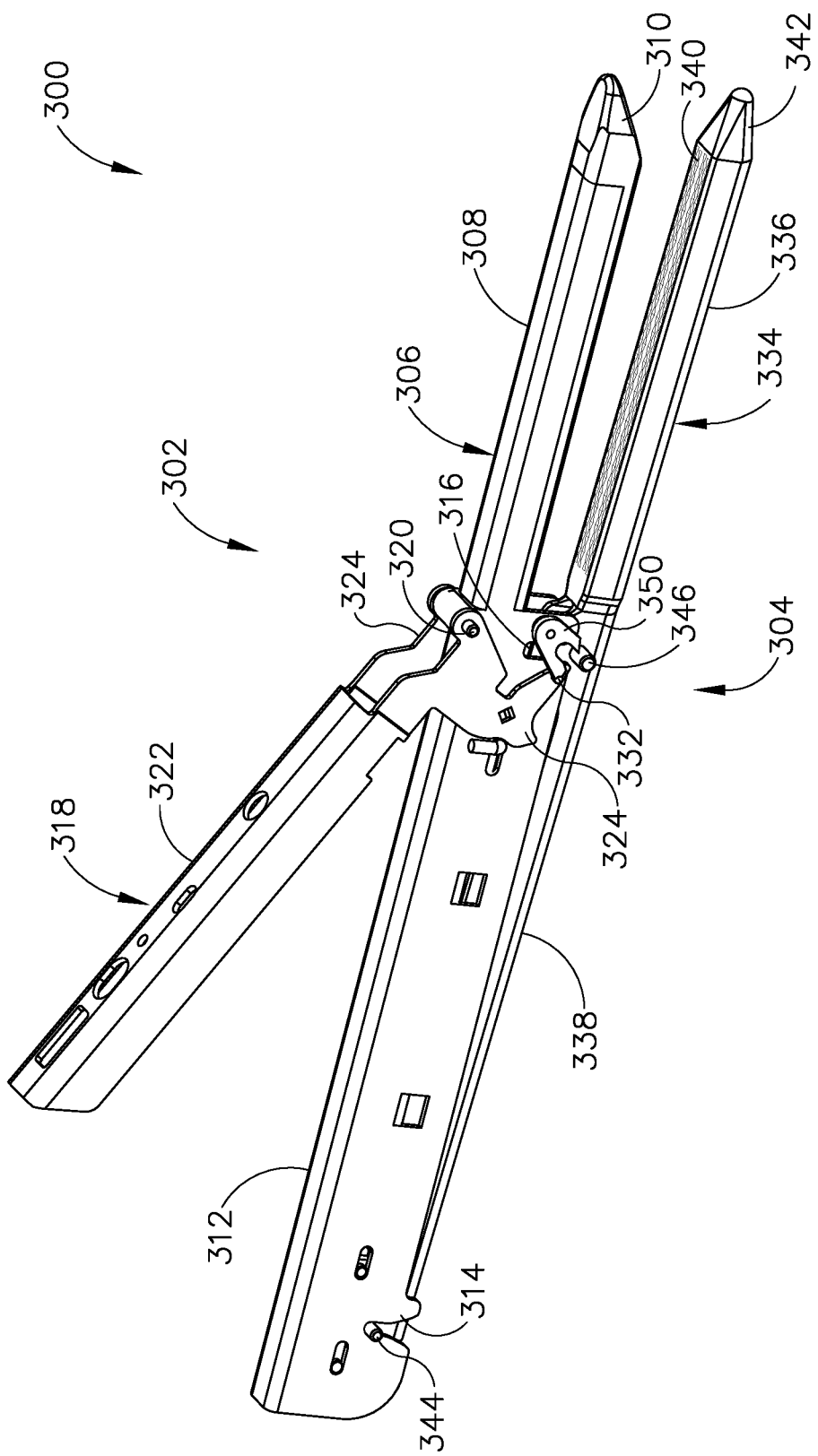
FIG. 12 depicts a perspective view of an exemplary surgical stapling instrument having a latch lockout member.
Figure 13A:
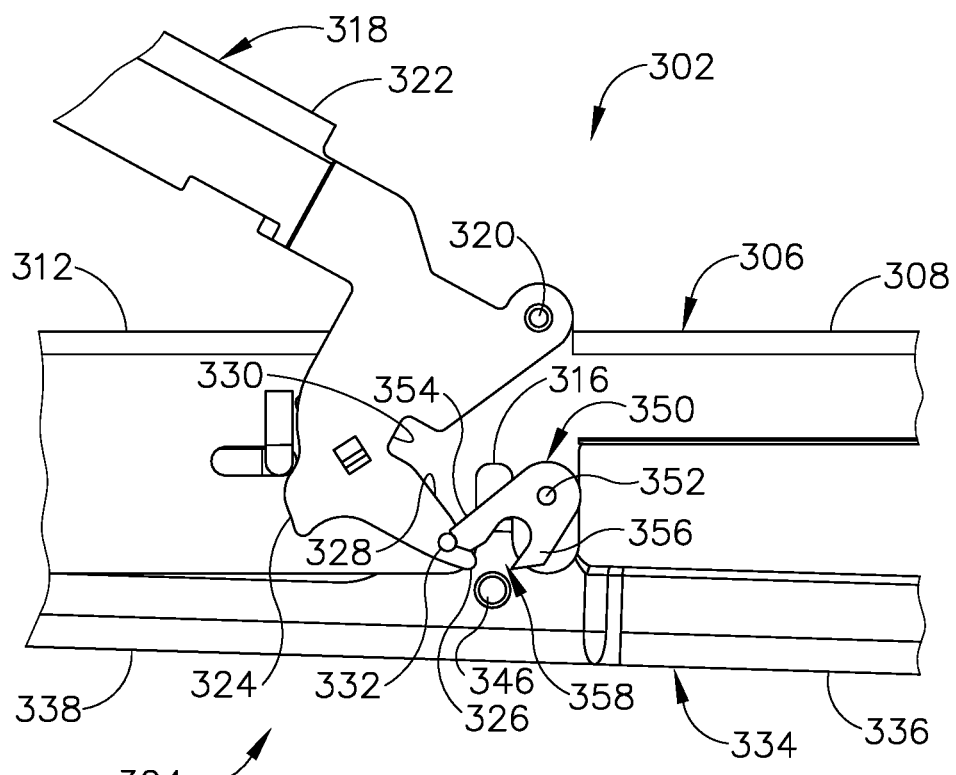
FIG. 13A depicts a partial side elevational view of the surgical instrument of FIG. 12, showing a latching lever of the instrument in an open position and the latch lockout member in a lockout state.
Figure 13B:
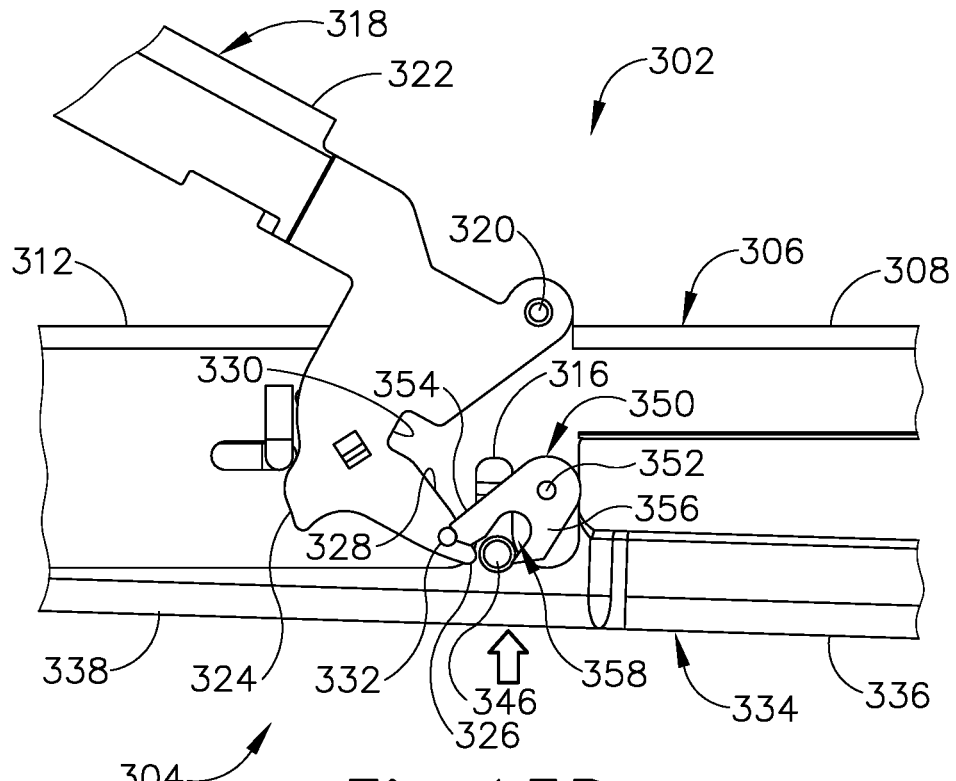
FIG. 13B depicts a partial side elevational view of the surgical instrument of FIG. 12, showing a latch pin of an anvil half of the instrument contacting the latch lockout member in the lockout state.
Figure 13C:
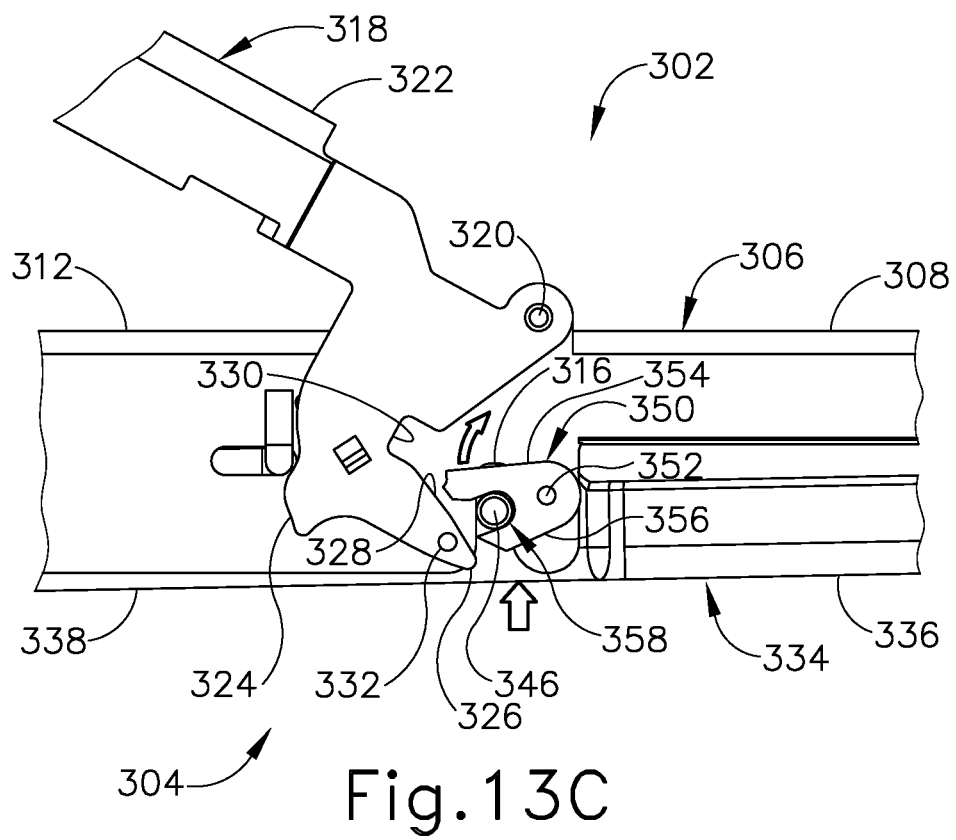
FIG. 13C depicts a partial side elevational view of the surgical instrument of FIG. 12, showing the latch lockout member in a release state and the latching lever in the open position.
Figure 13D:
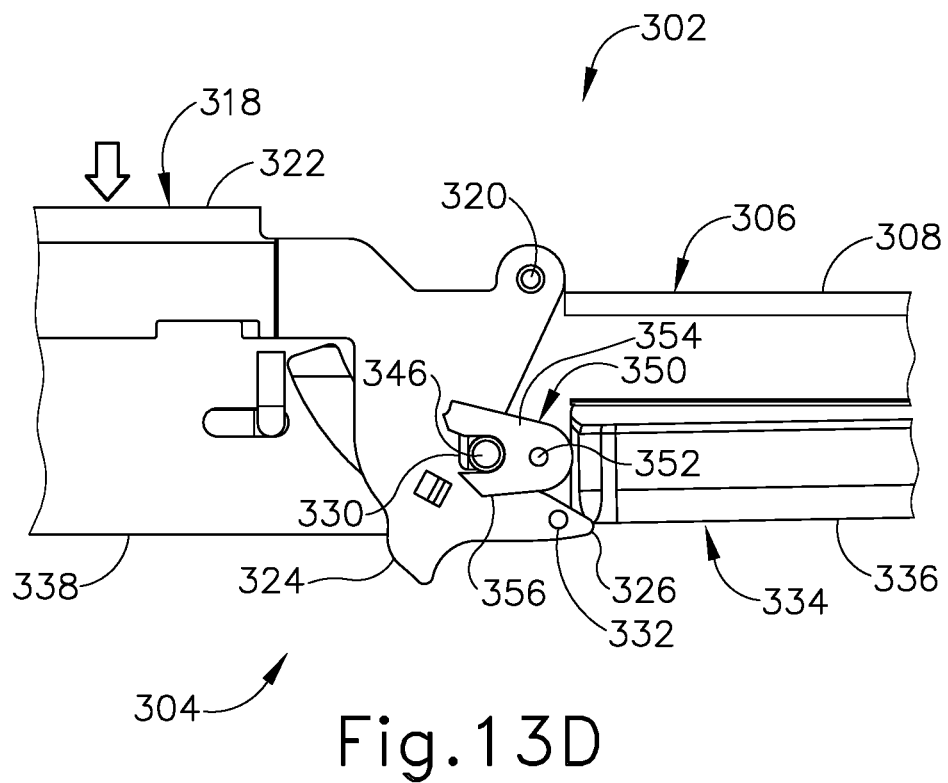
FIG. 13D depicts a partial side elevational view of the surgical instrument of FIG. 12, showing the latching lever in a closed position while the latch lockout member remains in the release state.

FIGS. 12-13D show another exemplary linear cutting stapler (300) that is similar to linear cutting stapler (100) described above except as otherwise described below. Stapler (300) includes a cartridge half (302) and an anvil half (304) configured to releasably couple together. Cartridge half (302) includes an elongate cartridge channel member (306) having a distal channel portion (308) configured to receive a staple cartridge (310), which may be similar to staple cartridge (150) described above. A proximal frame portion (312) of cartridge channel member (306) is configured to slidably retain components of a firing assembly (not shown), which may be similar to firing assembly (200) described above. As seen best in FIGS. 12 and 13A, cartridge channel member (306) further includes a first pair of slots (314) formed in opposed sidewalls at a proximal end of proximal frame portion (312), and a second pair of slots (316) formed in opposed sidewalls at a medial portion of cartridge channel member (306) near a distal end of proximal frame portion (312). Each slot (314, 316) extends transversely to a longitudinal axis of cartridge channel member (306) and opens to a side of cartridge half (302) that faces anvil half (304).

Cartridge half (302) further includes a closure lever in the form of latching lever (318) pivotably coupled to cartridge channel member (306) with a pivot pin (320) arranged at the medial portion of cartridge channel member (306). Latching lever (318) includes an elongate lever arm (322) and a pair of opposed jaws (324) extending distally from lever arm (322). As seen in FIG. 13A, each jaw (324) of the present example includes a distal tip (326), a camming surface (328), and a distally opening recess (330) configured to receive and capture a latch projection of anvil half (304), as described in greater detail below. Each jaw (324) further includes a protrusion (332), shown in the form of a post, extending laterally outward from a side face of jaw (324) at a location proximate to distal tip (326).

As seen in FIG. 12, anvil half (304) of linear cutting stapler (300) includes an elongate anvil channel member (334) having a distal channel portion (336) and a proximal frame portion (338). Distal channel portion (336) supports an anvil surface shown in the form of anvil plate (340), having a plurality of staple forming pockets, and a distal tip member (342) defining a distal end of anvil half (304). In other variations of stapler (300), the anvil surface may be formed integrally with or otherwise be rigidly connected to distal channel portion (336). In such variations, it will be appreciated that the anvil surface is still "supported by" distal channel portion (336). Proximal frame portion (338) defines a proximal end of anvil channel member (334) and supports a laterally extending pivot pin (344) at the proximal end. Opposed ends of pivot pin (344) are configured to be received within proximal slots (314) of cartridge channel member (306). Anvil channel member (334) is configured to pivot relative to cartridge channel member (306) about an axis defined by pivot pin (344). Proximal frame portion (338) of anvil half (304) is formed with a smaller lateral width than proximal frame portion (312) of cartridge channel member (306), such that proximal frame portion (338) may be received between opposed sidewalls of proximal frame portion (312).

Anvil half (304) further includes a pair of latch projections configured to be engaged by latching lever (318) of cartridge half (302). In the present example, the latch projections are defined by opposed ends of a latch pin (346) extending laterally through opposed sidewalls of anvil channel member (334) at a medial location between distal channel portion (336) and proximal frame portion (338). In other examples, the latch projections of stapler (300) may be similar to latch projections (131) described above. As described below, opposed ends of latch pin (346) are configured to be received within medial slots (316) of cartridge channel member (306). Though not shown, cartridge channel member (306), latching lever (318), and anvil channel member (334) may each include a cover similar to covers (108, 112, 186) described above, to facilitate gripping of stapler halves (302, 304) by an operator. It will be appreciated that various other features of stapler (100) described above may be incorporated in stapler (300) as well.

Similar to latching lever (180) described above, latching lever (318) is configured to pivot relative to cartridge channel member (306) between an open position (FIGS. 12-13C) and a closed position (FIG. 13D) to selectively clamp anvil half (304) against cartridge half (302) for clamping tissue therebetween. In the open position, latching lever (318) permits cartridge channel member (306) and anvil channel member (334) to move relative to one another. In the closed position, latching lever (318) captures the opposed ends of latch pin (346) within recesses (330) of lever jaws (324), thereby fixing channel members (306, 334) together to prevent relative movement between channel members (306, 334).

B. Exemplary Latch Lockout Feature of Linear Cutting Stapler

As best seen in FIG. 13A, cartridge half (302) of stapler (300) further includes a latch lockout member (350) pivotably to cartridge channel member (306) with a pivot pin (352). In the present example, latch lockout member (350) is positioned along the exterior of a lateral sidewall of the medial portion of cartridge channel member (306), and pivot pin (352) is positioned just distal to medial slots (316). As described below, latch lockout member (350) is configured to engage jaw (324) of latching lever (318). Though not shown, a second latch lockout member (350) may be positioned along the exterior of an opposed lateral sidewall of cartridge channel member (306) and configured to engage the opposed jaw (324) of latching lever (318).

Latch lockout member (350) of the present example is formed with a rounded V-like shape having a first leg (354), a second leg (356), and a cutout (358) defined therebetween. Lockout member (350) is configured to pivot about pivot pin (352) between a lockout state shown in FIGS. 13A and 13B, and a release state shown in FIGS. 13C and 13D. Additionally, lockout member (350) is suitably arranged on cartridge channel member (306) such that an open end of cutout (358) is oriented toward and aligns with an open end of the respective medial slot (316) of cartridge channel member (306) when lockout member (350) is in the lockout state.

To initially assume the lockout state, latching lever (318) is placed in the open position such that lever arm (322) is pivoted away from proximal frame portion (312) of cartridge channel member (306), and lever jaws (324) are pivoted away from medial slots (316). In the lockout state, an end surface of first leg (354) of lockout member (350) contacts a side surface of lateral protrusion (332) of the respective lever jaw (324), and thereby maintains latching lever (318) in the open position. This prevents lever jaws (324) from obstructing medial slots (316) of cartridge channel member (306), such that the opposed ends of latch pin (346) of anvil half (304) may be freely received within medial slots (316) as stapler halves (302, 304) are brought together, as shown in FIG. 13B.

As seen in FIGS. 12-13C, cartridge half (302) and anvil half (304) are brought together by directing proximal pivot pin (344) of anvil half (304) into proximal slots (314) of cartridge channel member (306), and then pivoting halves (302, 304) toward one another about proximal pivot pin (344). As seen in FIG. 13B, latch pin (346) of anvil half (304) is directed into medial slots (316) of cartridge channel member (306), past distal tips (326) of lever jaws (324), and into cutout (358) of lockout member (350). Continued pivoting of stapler halves (302, 304) toward one another causes latch pin (346) to contact a side surface of first leg (354) of lockout member (350). This contact causes lockout member (350) to pivot away from anvil half (304) such that first leg (354) disengages lateral protrusion (332) of lever jaw (324), as seen in FIG. 13C. This places lockout member (350) in a release state in which lockout member (350) is configured to freely pivot about its pivot pin (352), and latching lever (318) is configured to freely pivot about its pivot pin (320).

As seen in FIGS. 13C and 13D, the operator may then pivot lever arm (322) of latching lever (318) toward proximal frame portion (312) of cartridge channel member (306)

to engage latch pin (346) with camming surfaces (328) of lever jaws (324), and draw latch pin (346) deeper into medial slots (316) of cartridge channel member (306) and into jaw recesses (330). Simultaneously, latch lockout member (350) continues to pivot about its pivot pin (352) so as to rotate about latch pin (346), which remains disposed within cutout (358). Continued pivoting of latching lever (318) places it in the closed position in which latch pin (346) is captured within jaw recesses (330) such that cartridge and anvil channel members (306, 334) are fixed relative to one another. In the closed position of lever (318), as seen in FIG. 13D, jaws (324) capture a proximal side of latch pin (346) and lockout member (350) captures an opposed distal side of latch pin (346). In the present example, latch lockout member (350) is spaced laterally outward from cartridge channel member (306) such that lever jaw (324) is received in a space between lockout member (350) and a sidewall of cartridge channel member (306).

After a firing sequence is performed with stapler (300), latching lever (318) may be returned to the open position by pivoting lever arm (322) away from proximal frame portion (312) of cartridge channel member (306). This motion releases latch pin (346) from lever jaw (324) and simultaneously allows latch lockout member (350) to pivot back toward the lockout state in which first leg (354) reengages lateral protrusion (332) of lever jaw (324), thereby holding latching lever (318) in the open position. In some examples, latch lockout member (350) may be biased toward the lockout state by a resilient member (not shown).

As described above, latch lockout member (350) maintains latching lever (318) in the open position and allows latching lever (318) to pivot toward the closed position only in response to latch pin (346) being directed into medial slots (316) of cartridge channel member (306) to thereby contact lockout member (350). This prevents the undesirable scenario in which latching lever (318) might pivot out of the open position prematurely such that distal tips (326) of lever jaws (324) would obstruct medial slots (316) and prevent medial slots (316) from receiving latch pin (346). Furthermore, latch lockout member (350) in the lockout state is configured to maintain latching lever (318) in the open position securely enough that the operator can still exert a force on latching lever (318), for example to facilitate positioning of cartridge half (302) relative to anvil half (304) and tissue, without overcoming latch lockout member (350) and prematurely rotating lever (318). This may prove advantageous particularly when positioning stapler halves (302, 304) relative to thick tissue to be clamped.

III. Exemplary Linear Cutting Staplers Having Closure Mechanism that Provides Mechanical Advantage As described above in connection with staplers (100, 300), an operator clamps down on tissue positioned between distal portions of first and second halves of the stapler by pivoting the latching lever to a closed position. In some instances, particularly in surgical procedures involving thicker tissues, it can be difficult for the operator to apply the requisite closure force to the latching lever. This might require the operator to use both hands to close the latching lever in some cases. The exemplary staplers (400, 500) described below each include a closure mechanism that provides mechanical advantage to facilitate closure of the latching lever, thus enabling the operator to close the latching lever with a single hand, even in procedures involving relatively thick tissue, thereby enhancing ease of use of the stapler (400, 500).

Figure 14A:
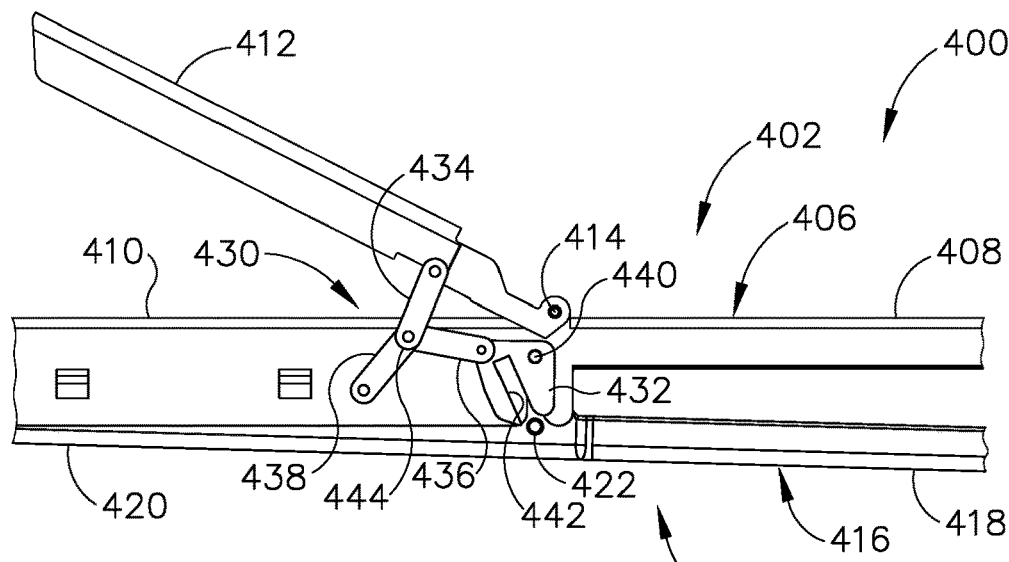
FIG. 14A depicts a side elevational view of an exemplary surgical stapling instrument having a closure mechanism that provides mechanical advantage to facilitate closure of a closure lever of the instrument for clamping tissue, showing the closure lever in an open position.
Figure 14B:
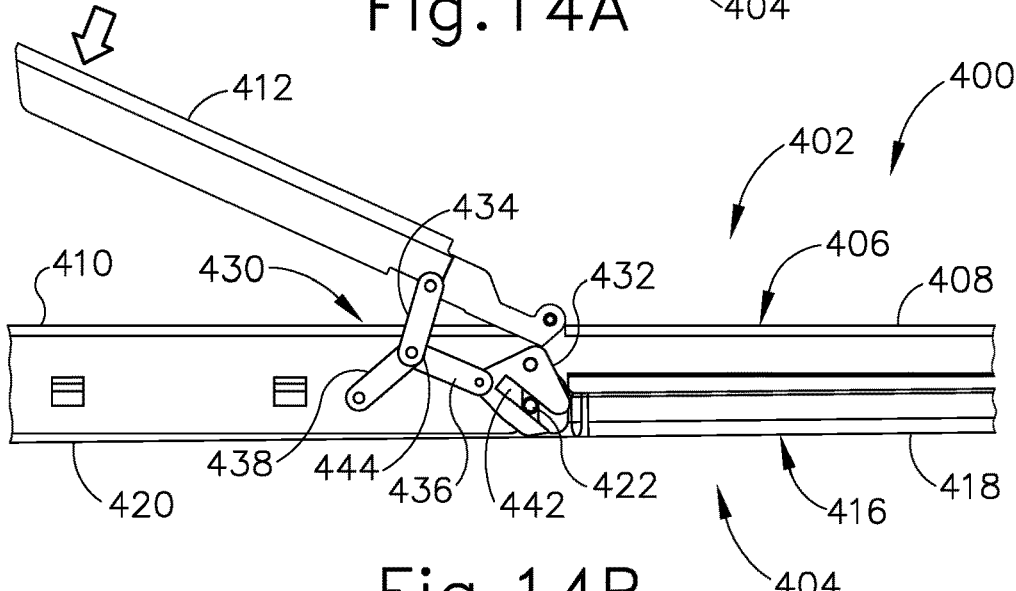
FIG. 14B depicts a side elevational view of the surgical instrument of FIG. 14A, showing the closure lever in a partially-closed position.
Figure 14C:
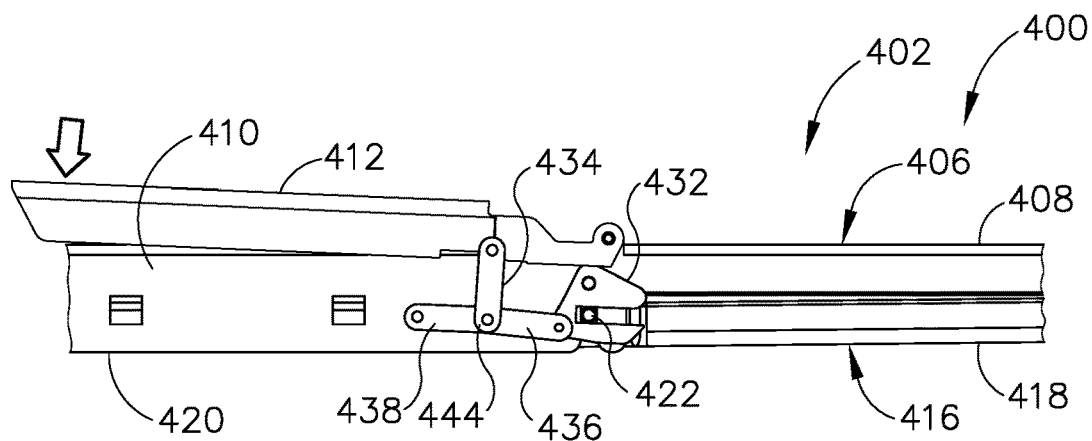
FIG. 14C depicts a side elevational view of the surgical instrument of FIG. 14A, showing the closure lever in a fully closed position.

A. Exemplary Stapler Having Closure Mechanism with First, Second, and Third Links FIGS. 14A-14C show an exemplary surgical stapler (400) that is substantially similar to stapler (100) described above except as otherwise described below. Stapler (400) includes a cartridge half (402) and an anvil half (404) configured to releasably couple together. Cartridge half (402) includes an elongate cartridge channel member (406) having a distal channel portion (408) and a proximal frame portion (410). Distal channel portion (408) is configured to receive a staple cartridge (not shown), which may be similar to staple cartridge (150) described above. Proximal frame portion (410) is configured to slidably house the components of a firing assembly (not shown), which may be similar to firing assembly (200) described above. Cartridge half (402) further includes a closure lever (412) that is pivotably coupled to cartridge channel member (406) with a pivot pin (414), and is movable between open and closed positions for releasably fixing stapler halves (402, 404) together, similar to latching levers (180, 318) described above. As described in greater detail below, closure lever (412) is operable to actuate components of a closure mechanism (430) that provides mechanical advantage by amplifying an input force applied to closure lever (412) by an operator.

Anvil half (404) of stapler (400) includes an elongate anvil channel member (416) having a distal channel portion (418) and a proximal frame portion (420). Distal channel portion (418) supports an anvil surface (not shown) having a plurality of staple forming pockets, and a distal tip member (not shown), which may be similar to anvil plate (134) and tip member (139) described above. Anvil half (404) further includes a pair of latch projections configured to be engaged by closure mechanism (430) of cartridge half (302). In the present example, the latch projections are defined by opposed ends of a latch pin (422) extending laterally through opposed sidewalls of a medial portion of anvil channel member (416).

As seen in FIG. 14A, closure mechanism (430) of stapler (400) includes a jaw member (432) and a plurality of links (434, 436, 438) that operatively couple jaw member (432) with closure lever (412). Jaw member (432) is pivotably coupled to the distal portion of a sidewall of proximal frame portion (410) of cartridge channel member (406) by a pivot pin (440). Jaw member (432) includes an elongate slot (442) configured to receive an end of latch pin (422) when lever (412) is pivoted toward a closed position, as described below. Links (434, 436, 438) are pivotably coupled together at a central joint (444) that is configured to float transversely relative to a longitudinal axis of cartridge channel member (406), in directions toward and away from anvil half (404) as described in greater detail below. First link (434) is pivotably coupled at a first end to a distal portion of closure lever (412), and at a second end to central joint (444). Second link (436) is pivotably coupled at a first end to a proximal end of jaw member (432), and at a second end to central joint (444). Third link (438) is pivotably coupled at a first end to a sidewall of proximal frame portion (410) of cartridge channel member (406), and at a second end to central joint (444). This arrangement of links (434, 436, 438) provides closure mechanism (430) with an "over-center" configuration in which first link (434) remains positioned over central joint (444) and offset proximally from jaw member (432) throughout actuation of closure mechanism (430), described below. While the illustrated example includes only one closure mechanism (430), variations of stapler (400) may include two closure mechanisms (430), with one closure mechanism (430) positioned on each side of cartridge channel member (406).

FIGS. 14A-14C show a closure sequence in which closure lever (412) is pivoted from an open position to a closed position to actuate links (434, 436, 438) of closure mechanism (430) and thereby capture latch pin (422) of anvil half (404) with jaw member (432) of cartridge half (402). As seen in FIGS. 14A and 14B, closure lever (412) is pivoted from the open position toward proximal frame portion (410) of cartridge channel member (406), which causes first link (434) to drive central joint (444) toward anvil channel member (416). This movement of central joint (444) causes third link (438) to pivot clockwise relative to cartridge channel member (406) and second link (436) to pivot counter-clockwise relative to jaw member (432). This motion of second link (436) causes jaw member (432) to also pivot counter-clockwise relative to cartridge channel member (406) so that jaw member (432) draws latch pin (422) of anvil half (404) proximally into slot (442), as seen in FIG. 14B. When closure lever (412) reaches the closed position, as seen in FIG. 14C, latch pin (422) is captured at a proximal end of jaw slot (442) and channel members (406, 416) are fixed relative to one another. With lever (412) in the closed position, first link (434) is arranged at approximately 90 degrees to each of second and third links (436, 438), which are approximately aligned with one another in colinear configuration. Closure lever (412) may be held in the closed position by an additional latch, a resilient member, or any other suitable mechanism that will be readily apparent to those of ordinary skill in the art.

The "over-center" configuration of closure mechanism (430) described above provides mechanical advantage that facilitates closure of lever (412) relative to cartridge channel member (406). In particular, an input force applied to lever (412) by an operator for closing lever (412) is amplified by closure mechanism (430) and then applied as an increased output force to latch pin (422) for drawing anvil half (404) into locking engagement with cartridge half (402). It will be understood that the same principle applies to an input force applied to lever (412) for opening lever (412) after a stapling operation has been performed. Advantageously, this enables an operator to more easily clamp and unclamp tissues of greater thicknesses while using only a single hand to actuate closure lever (412) between its open and closed positions.

B. Exemplary Stapler Having Closure Mechanism with Guide Slot

Figure 15A:
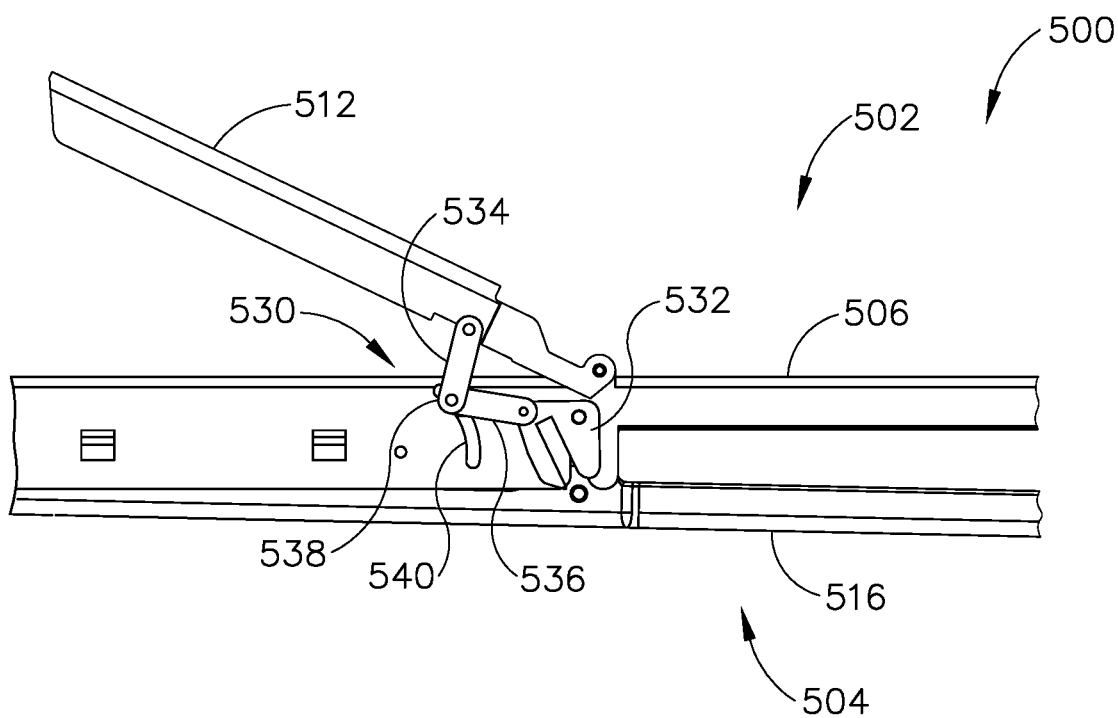
FIG. 15A depicts a side elevational view of another exemplary surgical stapling instrument having a closure mechanism that provides mechanical advantage to facilitate closure of a closure lever of the instrument, showing the latching lever in an open position.
Figure 15B:
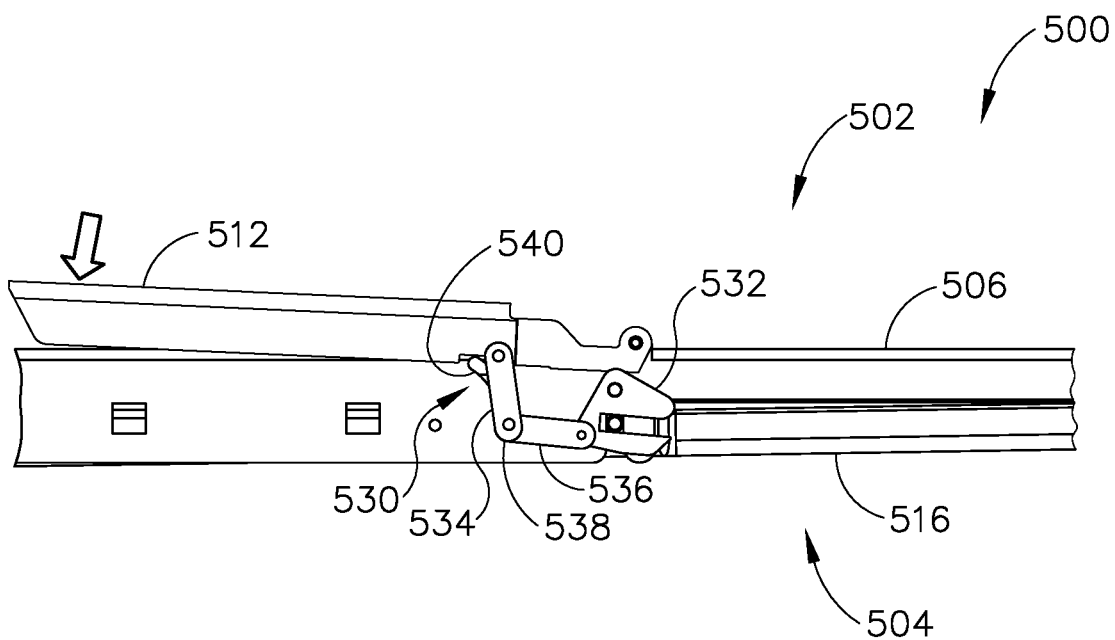
FIG. 15B depicts a side elevational view of the surgical instrument of FIG. 15A, showing the closure lever in a closed position.

FIGS. 15A and 15B show another exemplary surgical stapler (500) that is substantially similar to stapler (400) described above except as otherwise described below. Stapler (500) includes a cartridge half (502) and an anvil half (504) configured to releasably couple together. Cartridge half (502) includes a cartridge channel member (506) configured to receive a staple cartridge (not shown) and a closure lever (512) coupled to cartridge channel member (506). Anvil half (504) includes an anvil channel member (516) configured to support an anvil surface (not shown) having a plurality of staple forming pockets. Cartridge half (502) further includes a closure mechanism (530) having a jaw member (532) similar to jaw member (432) described above, and a plurality of links (534, 536) coupled together at a central joint (538) and which operatively couple jaw member (532) with closure lever (512). Closure mechanism (530) is substantially similar in structure and function to closure mechanism (430) described above, except as otherwise described below.

Closure mechanism (530) of stapler (500) differs from closure mechanism (430) of stapler (400) in that closure mechanism (530) includes only first and second links (534, 536). In place of third link (438), central joint (538) of closure mechanism (530) is configured to slide within a guide slot (540) formed in a sidewall of cartridge channel member (506). For instance, central joint (538) may include a protrusion (not shown) that is slidably received within guide slot (540). Guide slot (540) of the present example extends along an arcuate path that is generally transverse to a longitudinal axis of cartridge channel member (506). Guide slot (540) functions in a manner similar to third link (438) of closure mechanism (430) in that guide slot (540) constrains central joint (538) from a proximal side. Similar to closure mechanism (430), closure mechanism (530) provides a mechanical advantage that facilitates closure of closure lever (512), particularly for clamping across thick tissue.

IV. Exemplary Linear Cutting Stapler Having Ratcheting Closure Mechanism

In some surgical procedures, it may be difficult for the operator of a surgical stapler having first and second halves to fully clamp the halves together with a single motion of the closure lever, such as when clamping thicker tissues for example. Accordingly, it may be desirable to configure the closure mechanism of a surgical stapler so as to provide an initial gross-closure of the stapler halves, followed by a final fine-closure of the stapler halves. The exemplary surgical stapler (600) described below includes features that provide such functionality and thereby enhance ease of use for the operator.

FIGS. 16A-16D show an exemplary surgical stapler (600) that is similar to stapler (100) described above except as otherwise described below. Stapler (600) includes a cartridge half (602) and an anvil half (604). In the present example, stapler halves (602, 604) are non-releasably coupled together at their proximal ends by a pivot pin (605). In other examples, stapler halves (602, 604) may be configured to releasably couple together at their proximal ends, for instance in a manner similar those described above in connection with staplers (100, 300).

Cartridge half (602) includes an elongate cartridge channel member (606) having a distal channel portion (608) and a proximal frame portion (not shown). Distal channel portion (608) is configured to receive a staple cartridge (not shown), which may be similar to staple cartridge (150) described above. The proximal frame portion is shrouded by a first cover (610) and is configured to slidably house the components of a firing assembly (not shown), which may be similar to firing assembly (200) described above. Cartridge half (602) further includes a closure lever (612) that is pivotably coupled to cartridge channel member (606) and is movable between an open position (FIG. 16A) and a closed position (FIG. 16C) for releasably fixing stapler halves (602, 604) together, similar to closure levers (180, 318, 412, 512) described above. As described in greater detail below, closure lever (612) is operable to actuate a ratcheting closure mechanism (630) configured to draw stapler halves (602, 604) together toward a fully clamped state.

In the present example, closure lever (612) is biased toward the open position by a resilient member shown in the form of a torsion spring (614) arranged between closure lever (612) and first cover (610). Additionally, closure lever (612) is configured to be releasably locked in the closed position by snap fit engagement of a projection (616) formed on a proximal end of closure lever (612) with a receiving structure (618) formed on a confronting surface of first cover (610). The snap fit engagement of projection (616) with receiving structure (618) is sufficient to overcome the spring force exerted by torsion spring (614) when closure lever (612) is pivoted to the closed position by an operator.

Anvil half (604) of stapler (600) includes an elongate anvil channel member (620) having a distal channel portion (622) and a proximal frame portion (not shown). Distal channel portion (622) supports an anvil plate (not shown) and a distal tip member (not shown), which may be similar to anvil plate (134) and tip member (139) described above. The proximal frame portion of anvil channel member (620) is shrouded by a second cover (624).

Ratcheting closure mechanism (630) of stapler (600) is defined by a gear structure (632) provided by a pivoting distal end of closure lever (612), and a rack structure (634) coupled to and projecting transversely away from anvil half (604) in a direction toward cartridge half (602). Gear structure (632) includes a first arrangement of teeth (636) spaced circumferentially along at least a distally facing surface of gear structure (632), and rack structure (634) includes a second arrangement of teeth (638) arranged linearly along a proximally facing side of rack structure (634). Rack structure (634) is positioned just distally of gear structure (632) such that gear teeth (636) are positioned to engage rack teeth (638).

Figure 16A:
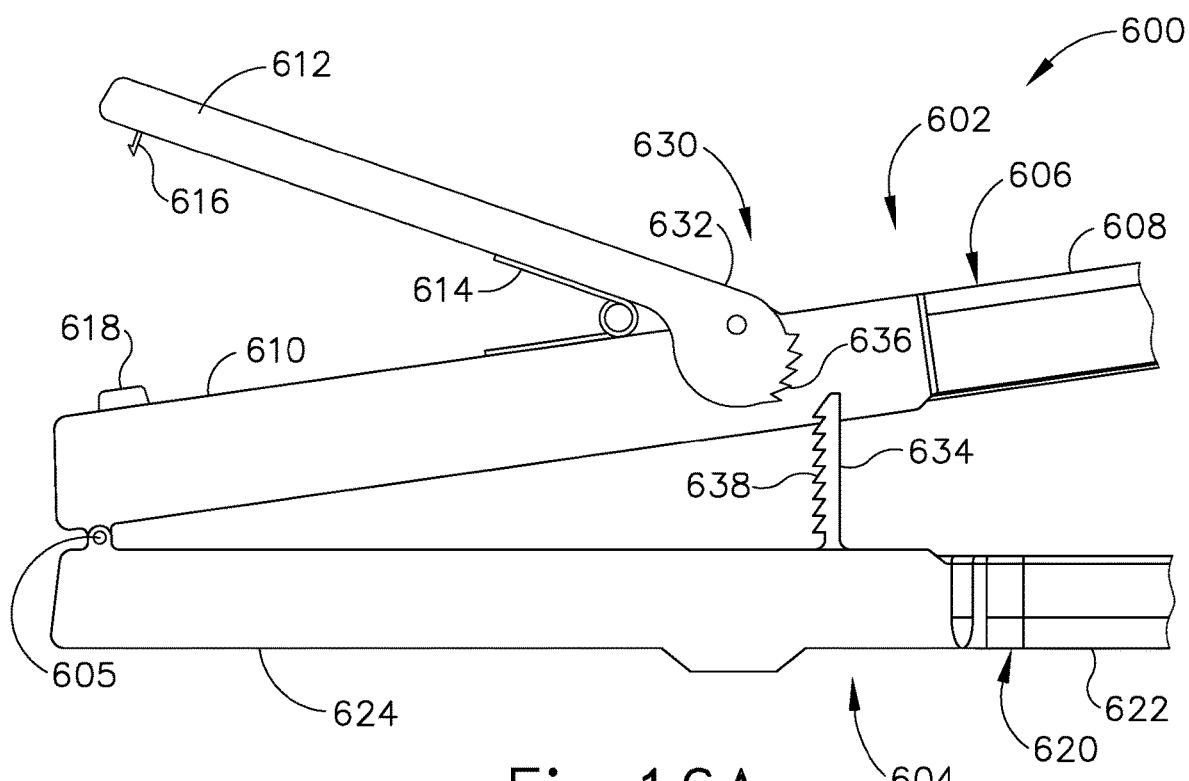
FIG. 16A depicts a side elevational view of an exemplary surgical stapling instrument having a ratchet closure mechanism, showing a cartridge half of the instrument in a first position relative to an anvil half and a closure lever in an open position.
Figure 16B:
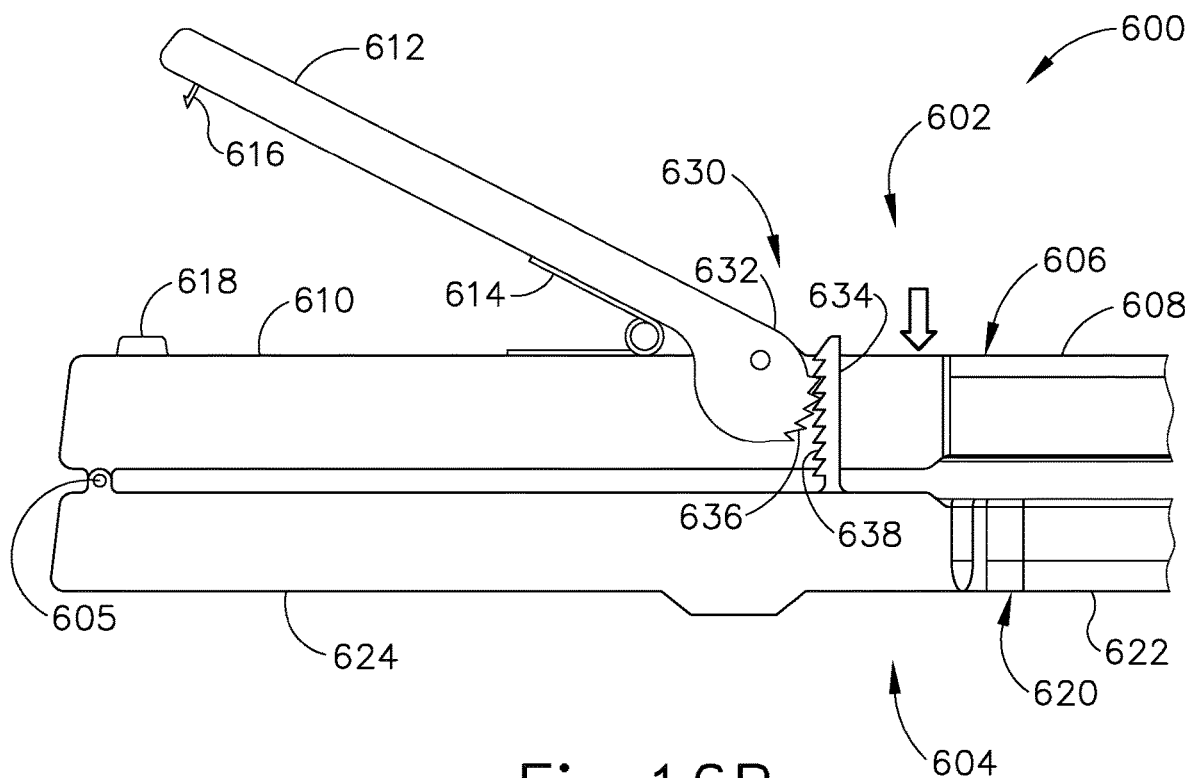
FIG. 16B depicts a side elevational view of the surgical instrument of FIG. 16A, showing the cartridge half in a second position relative to the anvil half in which components the ratcheting mechanism engage one another, with the closure lever remaining in the open position.

As seen in FIGS. 16A and 16B, stapler halves (602, 604) are configured to pivot toward one another about proximal pivot pin (605) between an unclamped state (FIG. 16A) and a partially-clamped state (FIG. 16B), during which closure lever (612) remains stationary in the open position. As stapler halves (602, 604) pivot toward the partially-clamped state of FIG. 16B, gear teeth (636) of gear structure (632) slide over rack teeth (638) of rack structure (634) in a ratcheting fashion. In that regard, gear teeth (636) and/or rack teeth (638) may be swept in a suitable direction that enables teeth (636, 638) to slip past one another as stapler halves (602, 604) are pivoted toward one another, but lockingly engage one another to prevent stapler halves (602, 604) from being pivoted away from one another. For instance, gear teeth (636) may be swept in a direction toward cartridge half (602), and/or rack teeth (638) may be swept in a direction toward anvil half (604). The transition of stapler halves (602, 604) from the unclamped state (FIG. 16A) to the partially-clamped state (FIG. 16B) provides an initial gross-closure of stapler halves (602, 604) for partially clamping tissue positioned therebetween.

Figure 16C:
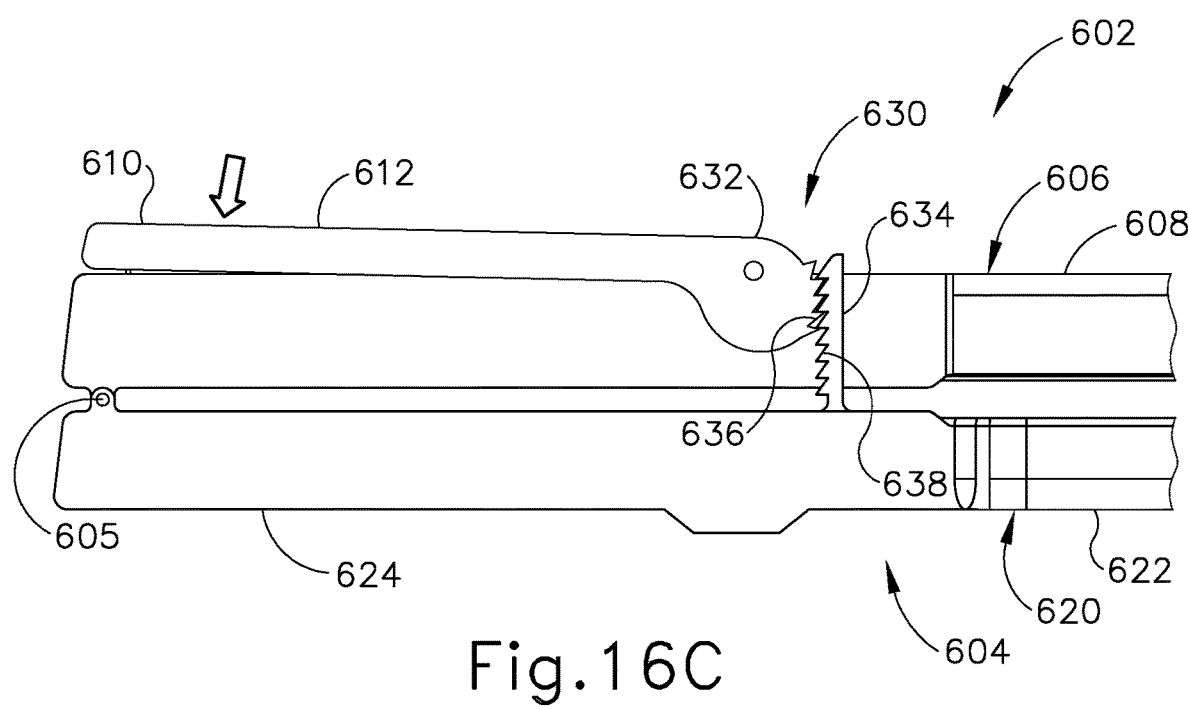
FIG. 16C depicts a side elevational view of the surgical instrument of FIG. 16A, showing the closure lever in a closed position for clamping tissue.

FIG. 16C shows pivoting of closure lever (612) from the open position to the closed position following the initial gross-closure step described above. This step provides a final, fine-closure of stapler halves (602, 604) for fully clamping tissue positioned therebetween. In particular, pivoting closure lever (612) toward the closed position causes gear teeth (636) to lockingly engage rack teeth (638) and thereby drive stapler halves (602, 604) closer toward one another into a fully-clamped state. Though not shown, closure mechanism (630) may additionally include a camming feature that facilitates the drawing of stapler halves (602, 604) into the fully-clamped state. As closure lever (612) reaches the closed position shown in FIG. 16C, lever projection (616) is received within receiving structure (618) with a snap fit engagement, which maintains closure lever (612) in the closed position.

Figure 16D:
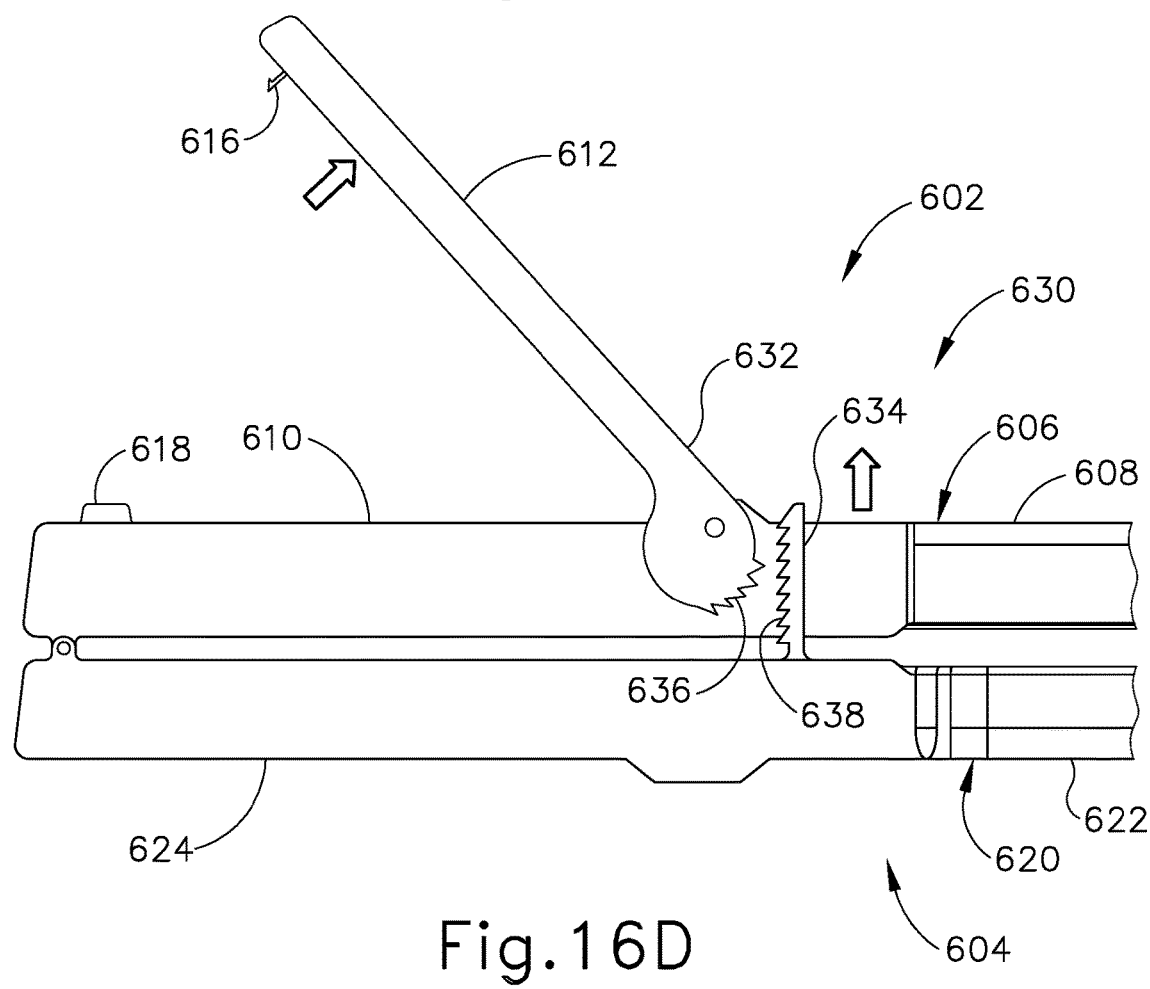
FIG. 16D depicts a side elevational view of the surgical instrument of FIG. 16A, showing the closure lever in an open position that disengages the components of the ratcheting mechanism so the instrument halves can be separated from one another.

FIG. 16D shows reopening of closure lever (612) when the operator wishes to separate stapler halves (602, 604) after stapler (600) is fired. The operator pulls on a proximal end of closure lever (612) to disengage the snap fit engagement between lever projection (616) and receiving structure (618). The operator then pivots lever (612) toward the open position so that gear teeth (636) of gear structure (632) disengage rack teeth (638) of rack structure (634). This disengagement of teeth (636, 638) allows stapler halves (602, 604) to be pivoted away from one another.

The configuration of ratcheting closure mechanism (630) described above enables an operator to easily achieve a secure and proper clamping of tissue with stapler halves (602, 604). For instance, ratcheting closure mechanism (630) provides for a partially-clamped state in addition to a fully-clamped state, which accommodates any final positional adjustments of tissue relative to stapler halves (602, 604). Additionally, the distance by which the proximal end of closure lever (612) is spaced from anvil half (604) when in the open position is generally less than that of other staplers with a configuration similar to stapler (100). This reduces the grip span of stapler (600) and thus enables an operator to more easily grip stapler (600) and actuate closure lever (612) with a single hand. The configuration of ratcheting closure mechanism (630) may also reduce the force that an operator must apply to closure lever (612) to achieve a fully-clamped state.

V. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler, comprising: (a) an anvil channel member; (b) an anvil surface having a plurality of staple forming pockets; (c) a cartridge channel member configured to releasably couple with the anvil channel member, wherein a distal portion of the cartridge channel member is configured to receive a staple cartridge; (d) a first latch feature; (e) a second latch feature, wherein the second latch feature is movable between an open position in which the anvil channel member and the cartridge channel member are moveable relative to one another, and a closed position in which the second latch feature engages the first latch feature and thereby fixes the anvil channel member and the cartridge channel member relative to one another; and (f) a latch lockout member, wherein the latch lockout member is movable between a lockout state in which the latch lockout member locks the second latch feature in the open position, and a release state in which the latch lockout member permits the second latch feature to move from the open position to the closed position, wherein the latch lockout member is configured to move from the lockout state to the release state in response to being engaged by the first latch feature.

Example 2

The surgical stapler of Example 1, wherein the first latch feature is coupled to the anvil channel member, wherein the second latch feature is coupled to the cartridge channel member.

Example 3

The surgical stapler of any of the preceding Examples, wherein the first latch feature comprises a latch projection, wherein the second latch feature comprises a latching lever pivotably coupled to the cartridge channel member, wherein the latching lever includes a jaw configured to capture the latch projection when the latching lever is in the closed position.

Example 4

The surgical stapler of any of the preceding Examples, wherein the latch lockout member is configured to engage the second latch feature in the lockout state to thereby prevent the second latch feature from contacting the first latch feature.

Example 5

The surgical stapler of any of the preceding Examples, wherein the latch lockout member is pivotably coupled to the cartridge channel member and is configured to pivot between the lockout state and the release state about a pivot axis.

Example 6

The surgical stapler of Example 5, wherein the pivot axis is located proximal to the distal portion of the cartridge channel member.

Example 7

The surgical stapler of any of the preceding Examples, wherein the second latch feature is configured to pivot between the open position and the closed position about a first pivot axis, wherein the latch lockout member is configured to pivot between the lockout state and the release state about a second pivot axis, wherein the second pivot axis is offset from and parallel to the first pivot axis.

Example 8

The surgical stapler of any of the preceding Examples, wherein the latch lockout member includes a first engagement surface configured to contact the first latch feature and a second engagement surface configured to contact the second latch feature, wherein the first latch feature is configured to contact the first engagement surface to thereby disengage the second engagement surface from the second latch feature and move the latch lockout member from the lockout state to the release state.

Example 9

The surgical stapler of Example 8, wherein the first latch feature is coupled to the anvil channel member, wherein cartridge channel member includes a slot configured to receive the first latch feature, wherein the first latch feature is configured to move the latch lockout member from the lockout state to the release state when the first latch feature is received within the slot.

Example 10

The surgical stapler of Example 9, wherein the latch lockout member includes a cutout feature that defines the first engagement surface, wherein the cutout feature is configured to align with the slot such that the first latch feature is receivable within the slot and the cutout feature simultaneously when the latch lockout member is in the lockout state.

Example 11

The surgical stapler of Example 10, wherein the latch lockout member is configured to rotate about the first latch feature when the first latch feature is disposed within the cutout feature.

Example 12

The surgical stapler of any of the preceding Examples, wherein the second latch feature includes a laterally extending protrusion, wherein the latch lockout member is configured to contact the laterally extending protrusion when in the lockout state to thereby lock the second latch feature in the open position.

Example 13

The surgical stapler of any of the preceding Examples, wherein when the second latch feature is in the closed position and the latch lockout member is in the release state, the first latch feature is configured to be captured by second latch feature and by the latch lockout member simultaneously.

Example 14

The surgical stapler of any of the preceding Examples, wherein the latch lockout member is configured to assume the lockout state in response to the second latch feature moving from the closed position to the open position.

Example 15

The surgical stapler of any of the preceding Examples, wherein the latch lockout member is positioned along the exterior of a lateral side portion of the cartridge channel member.

Example 16

A surgical stapler, comprising: (a) an anvil half comprising: (i) an anvil channel member, and (ii) an anvil surface having a plurality of staple forming pockets; and (b) a cartridge half configured to releasably couple with the anvil half, wherein the cartridge half comprises: (i) a cartridge channel member having a distal portion configured to receive a staple cartridge, (ii) a latching lever pivotably coupled to the cartridge channel member, wherein the latching lever is pivotable between an open position in which the latching lever permits movement of the anvil channel member relative to the cartridge channel member, and a closed position in which the latching lever fixes the anvil channel member relative to the cartridge channel member, and (iii) a latch lockout member movably coupled to a lateral side portion of the cartridge channel member, wherein the latch lockout member is movable between a lockout state in which the latch lockout member locks the latching lever in the open position, and a release state in which the latch lockout member permits the latching lever to pivot from the open position to the closed position.

Example 17

The surgical stapler of Example 16, wherein the latch lockout member is configured to move from the lockout state to the release state in response to being engaged by a portion of the anvil half.

Example 18

The surgical stapler of any of Examples 16 through 17, wherein the latching lever includes a lever arm and is pivotably coupled to the cartridge channel member about a first pivot axis, wherein the latch lockout member is pivotably coupled to the cartridge channel member about a second pivot axis, wherein the second pivot axis is offset from the first pivot axis and is positioned distal to the lever arm.

Example 19

A surgical stapler, comprising: (a) an anvil half comprising: (i) an anvil channel member, and (ii) an anvil surface having a plurality of staple forming pockets, (b) a cartridge half configured to releasably couple with the anvil half, wherein the cartridge half comprises: (i) a cartridge channel member having a distal portion configured to receive a staple cartridge, (ii) a latching member movably coupled to the cartridge channel member, wherein the latching member is movable between an open position in which the latching member permits movement of the anvil channel member relative to the cartridge channel member, and a closed position in which the latching member fixes the anvil channel member relative to the cartridge channel member; and (c) a latch lockout member positioned to engage the anvil half, wherein the latch lockout member is configured to pivot between a lockout state in which the latch lockout member locks the latching member in the open position, and a release state in which the latch lockout member permits the latching member to move from the open position to the closed position, wherein the latch lockout member is configured to move from the lockout state to the release state in response to being engaged by the anvil half.

Example 20

The surgical stapler of Example 19, wherein the latch lockout member is pivotably coupled to the cartridge channel member.

VI. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed Feb. 6, 2018, published as U.S. Pat. Pub. No. 2019/0239881 on Aug. 8, 2019; U.S. application Ser. No. 15/889,370, entitled "Lockout Assembly for Linear Surgical Stapler," filed Feb. 6, 2018, published as U.S. Pat. Pub. No. 2019/0239882 on Aug. 8, 2019; U.S. application Ser. No. 15/889,374, entitled "Features to Align and Close Linear Surgical Stapler," filed Feb. 6, 2018, published as U.S. Pat. Pub. No. 2019/0239886 on Aug. 8, 2019; U.S. application Ser. No. 15/889,376, entitled "Releasable Coupling Features for Proximal Portions of Linear Surgical Stapler," filed Feb. 6, 2018, published as U.S. Pat. Pub. No. 2019/0239883 on Aug. 8, 2019; and U.S. application Ser. No. 15/889,388, entitled "Firing Lever Assembly for Linear Surgical Stapler," filed Feb. 6, 2018, published as U.S. Pat. Pub. No. 2019/0239884 on Aug. 8, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler, comprising:
(a) an anvil channel member;
(b) an anvil surface having a plurality of staple forming pockets;
(c) a cartridge channel member configured to releasably couple with the anvil channel member, wherein a distal portion of the cartridge channel member is configured to receive a staple cartridge;
(d) a first latch feature;
(e) a second latch feature, wherein the second latch feature is movable between an open position in which the anvil channel member and the cartridge channel member are moveable relative to one another, and a closed position in which the second latch feature engages the first latch feature and thereby fixes the anvil channel member and the cartridge channel member relative to one another; and
(f) a latch lockout member, wherein the latch lockout member is movable relative to the first and second latch features between a lockout state in which the latch lockout member locks the second latch feature in the open position, and a release state in which the latch lockout member permits the second latch feature to move from the open position to the closed position, wherein the latch lockout member moves from the lockout state to the release state in response to being engaged by the first latch feature.

2. The surgical stapler of claim 1, wherein the first latch feature is coupled to the anvil channel member, wherein the second latch feature is coupled to the cartridge channel member.

3. The surgical stapler of claim 2, wherein the first latch feature comprises a latch projection, wherein the second latch feature comprises a latching lever pivotably coupled to the cartridge channel member, wherein the latching lever includes a jaw configured to capture the latch projection when the latching lever is in the closed position.

4. The surgical stapler of claim 1, wherein the latch lockout member is configured to engage the second latch feature in the lockout state to thereby prevent the second latch feature from contacting the first latch feature.

5. The surgical stapler of claim 1, wherein the latch lockout member is pivotably coupled to the cartridge channel member and is configured to pivot between the lockout state and the release state about a pivot axis.

6. The surgical stapler of claim 5, wherein the pivot axis is located proximal to the distal portion of the cartridge channel member.

7. The surgical stapler of claim 1, wherein the second latch feature is configured to pivot between the open position and the closed position about a first pivot axis, wherein the latch lockout member is configured to pivot between the lockout state and the release state about a second pivot axis, wherein the second pivot axis is offset from and parallel to the first pivot axis.

8. The surgical stapler of claim 1, wherein the latch lockout member includes a first engagement surface configured to contact the first latch feature and a second engagement surface configured to contact the second latch feature, wherein the first latch feature is configured to contact the first engagement surface to thereby disengage the second engagement surface from the second latch feature and move the latch lockout member from the lockout state to the release state.

9. The surgical stapler of claim 8, wherein the first latch feature is coupled to the anvil channel member, wherein cartridge channel member includes a slot configured to receive the first latch feature, wherein the first latch feature is configured to move the latch lockout member from the lockout state to the release state when the first latch feature is received within the slot.

10. The surgical stapler of claim 9, wherein the latch lockout member includes a cutout feature that defines the first engagement surface, wherein the cutout feature is configured to align with the slot such that the first latch feature is receivable within the slot and the cutout feature simultaneously when the latch lockout member is in the lockout state.

11. The surgical stapler of claim 10, wherein the latch lockout member is configured to rotate about the first latch feature when the first latch feature is disposed within the cutout feature.

12. The surgical stapler of claim 1, wherein the second latch feature includes a laterally extending protrusion, wherein the latch lockout member is configured to contact the laterally extending protrusion when in the lockout state to thereby lock the second latch feature in the open position.

13. The surgical stapler of claim 1, wherein when the second latch feature is in the closed position and the latch lockout member is in the release state, the first latch feature is configured to be captured by second latch feature and by the latch lockout member simultaneously.

14. The surgical stapler of claim 1, wherein the latch lockout member is configured to assume the lockout state in response to the second latch feature moving from the closed position to the open position.

15. The surgical stapler of claim 1, wherein the latch lockout member is positioned along the exterior of a lateral side portion of the cartridge channel member.

16. A surgical stapler, comprising:
(a) an anvil half comprising:
(i) an anvil channel member, and
(ii) an anvil surface having a plurality of staple forming pockets; and (b) a cartridge half configured to releasably couple with the anvil half, wherein the cartridge half comprises:
  (i) a cartridge channel member having a distal portion configured to receive a staple cartridge,
  (ii) a latching lever pivotably coupled to the cartridge channel member, wherein the latching lever is pivotable between an open position in which the latching lever permits movement of the anvil channel member relative to the cartridge channel member, and a closed position in which the latching lever fixes the anvil channel member relative to the cartridge channel member, and
  (iii) a latch lockout member movably coupled to the cartridge channel member, wherein the latch lockout member is movable relative to the latching lever between a lockout state in which the latch lockout member locks the latching lever in the open position, and a release state in which the latch lockout member permits the latching lever to pivot from the open position to the closed position.

17. The surgical stapler of claim 16, wherein the latch lockout member is configured to move from the lockout state to the release state in response to being engaged by a portion of the anvil half.

18. The surgical stapler of claim 16, wherein the latching lever includes a lever arm and is pivotably coupled to the cartridge channel member about a first pivot axis, wherein the latch lockout member is pivotably coupled to the cartridge channel member about a second pivot axis, wherein the second pivot axis is offset from the first pivot axis and is positioned distal to the lever arm.

19. A surgical stapler, comprising:
(a) an anvil half comprising:
  (i) an anvil channel member, and
  (ii) an anvil surface having a plurality of staple forming pockets,
(b) a cartridge half configured to releasably couple with the anvil half, wherein the cartridge half comprises:
  (i) a cartridge channel member having a distal portion configured to receive a staple cartridge,
  (ii) a latching member movably coupled to the cartridge channel member, wherein the latching member is movable between an open position in which the latching member permits movement of the anvil channel member relative to the cartridge channel member, and a closed position in which the latching member fixes the anvil channel member relative to the cartridge channel member; and
(c) a latch lockout member positioned to engage the anvil half, wherein the latch lockout member is movable relative to the latching member between a lockout state in which the latch lockout member locks the latching member in the open position, and a release state in which the latch lockout member permits the latching member to move from the open position to the closed position,
wherein the latch lockout member moves from the lockout state to the release state in response to being engaged by the anvil half.

20. The surgical stapler of claim 19, wherein the latch lockout member is pivotably coupled to the cartridge channel member and is configured to pivot between the lockout state and the release state.

* * * * *